United States Patent
Blain et al.

(10) Patent No.: US 10,426,524 B2
(45) Date of Patent: Oct. 1, 2019

(54) APPARATUS FOR SPINAL FIXATION AND METHODS OF USE

(71) Applicant: Spinal Elements, Inc., Carlsbad, CA (US)

(72) Inventors: Jason Blain, Encinitas, CA (US); Greg Martin, Carlsbad, CA (US)

(73) Assignee: Spinal Elements, Inc., Carlsbad, CA (US)

(*) Notice: Subject to any disclaimer, the term of this patent is extended or adjusted under 35 U.S.C. 154(b) by 0 days.

(21) Appl. No.: 15/784,577

(22) Filed: Oct. 16, 2017

(65) Prior Publication Data

US 2018/0085149 A1     Mar. 29, 2018

Related U.S. Application Data

(62) Division of application No. 13/804,407, filed on Mar. 14, 2013, now Pat. No. 9,820,784.

(51) Int. Cl.
*A61B 17/70* (2006.01)

(52) U.S. Cl.
CPC ...... *A61B 17/7068* (2013.01); *A61B 17/7053* (2013.01)

(58) Field of Classification Search
CPC . A61B 17/7068; A61B 17/7053; A61B 17/56; A61B 2017/564
See application file for complete search history.

(56) References Cited

U.S. PATENT DOCUMENTS

| | | |
|---|---|---|
| 86,016 A | 1/1869 | Howell |
| 1,630,239 A | 5/1927 | Binkley et al. |
| 1,822,280 A | 9/1931 | Ervay |
| 1,822,330 A | 9/1931 | Anslie |
| 2,486,303 A | 10/1949 | Longfellow |
| 2,706,023 A | 4/1955 | Merritt |
| 2,967,282 A | 1/1961 | Schwartz et al. |
| 3,111,945 A | 11/1963 | Von Solbrig |
| 3,149,808 A | 9/1964 | Weckesser |

(Continued)

FOREIGN PATENT DOCUMENTS

| | | |
|---|---|---|
| CA | 2 437 575 | 4/2009 |
| DE | 93 04 368 | 5/1993 |

(Continued)

OTHER PUBLICATIONS

3rd Party Lab Notebook, "Facet Cartilage Repair," dated May 20, 2003 in 2 pages.

(Continued)

*Primary Examiner* — Ellen C Hammond
(74) *Attorney, Agent, or Firm* — Knobbe, Martens, Olson & Bear, LLP

(57) ABSTRACT

In some embodiments, a method comprises forming a lumen in a first bone portion and forming a lumen in a second bone portion. The method further includes inserting a portion of a flexible fastening band through the lumen in the first bone portion and through the lumen in the second bone portion, and inserting the portion of the flexible fastening band into a fastener mechanism monolithically formed with the flexible fastening band. The method further includes advancing the portion of the flexible fastening band through the fastener mechanism until the first bone portion and the second bone portion are stabilized.

18 Claims, 14 Drawing Sheets

(56) References Cited

U.S. PATENT DOCUMENTS

| | | |
|---|---|---|
| 3,570,497 A | 3/1971 | Lemole |
| 3,867,728 A | 2/1975 | Stubstad et al. |
| 3,875,595 A | 4/1975 | Froning |
| 3,879,767 A | 4/1975 | Stubstad |
| 4,001,896 A | 1/1977 | Arkangel |
| 4,037,603 A | 7/1977 | Wendorff |
| 4,085,466 A | 4/1978 | Goodfellow et al. |
| 4,119,091 A | 10/1978 | Partridge |
| 4,156,296 A | 5/1979 | Johnson et al. |
| 4,164,793 A | 8/1979 | Swanson |
| 4,231,121 A | 11/1980 | Lewis |
| D261,935 S | 11/1981 | Halloran |
| 4,312,337 A | 1/1982 | Donohue |
| 4,323,217 A | 4/1982 | Dochterman |
| 4,349,921 A | 9/1982 | Kuntz |
| 4,502,161 A | 3/1985 | Wall |
| D279,502 S | 7/1985 | Halloran |
| D279,503 S | 7/1985 | Halloran |
| 4,535,764 A | 8/1985 | Ebert |
| 4,573,458 A | 3/1986 | Lower |
| 4,573,459 A | 3/1986 | Litton |
| 4,634,445 A | 1/1987 | Helal |
| 4,662,371 A | 5/1987 | Whipple et al. |
| 4,706,659 A | 11/1987 | Matthews et al. |
| 4,714,469 A | 12/1987 | Kenna |
| 4,722,331 A | 2/1988 | Fox |
| 4,730,615 A | 3/1988 | Sutherland et al. |
| 4,759,766 A | 7/1988 | Buettner-Janz et al. |
| 4,759,769 A | 7/1988 | Hedman et al. |
| 4,772,287 A | 9/1988 | Ray et al. |
| 4,773,402 A | 9/1988 | Asher et al. |
| 4,834,757 A | 5/1989 | Brantigan |
| 4,863,477 A | 9/1989 | Monson |
| 4,904,260 A | 2/1990 | Ray et al. |
| 4,907,577 A | 3/1990 | Wu |
| 4,911,718 A | 3/1990 | Lee et al. |
| 4,919,667 A | 4/1990 | Richmond |
| 4,923,471 A | 5/1990 | Morgan |
| 4,936,848 A | 6/1990 | Bagby |
| 4,941,466 A | 7/1990 | Romano |
| 4,959,065 A | 9/1990 | Arnett et al. |
| 4,969,909 A | 11/1990 | Barouk |
| 5,000,165 A | 3/1991 | Watanabe |
| 5,002,546 A | 3/1991 | Romano |
| 5,011,484 A | 4/1991 | Bréard |
| 5,015,255 A | 5/1991 | Kuslich |
| 5,047,055 A | 9/1991 | Bao et al. |
| 5,062,845 A | 11/1991 | Kuslich |
| 5,071,437 A | 12/1991 | Steffee |
| 5,092,866 A | 3/1992 | Breard et al. |
| 5,112,013 A | 5/1992 | Tolbert et al. |
| 5,112,346 A | 5/1992 | Hiltebrandt et al. |
| 5,127,912 A | 7/1992 | Ray et al. |
| 5,135,188 A | 8/1992 | Anderson et al. |
| 5,147,404 A | 9/1992 | Downey |
| 5,171,280 A | 12/1992 | Baumgartner |
| 5,192,326 A | 3/1993 | Bao et al. |
| 5,192,327 A | 3/1993 | Brantigan |
| 5,209,755 A | 5/1993 | Abrahan et al. |
| 5,258,031 A | 11/1993 | Salib et al. |
| 5,282,861 A | 2/1994 | Kaplan |
| 5,286,249 A | 2/1994 | Thibodaux |
| 5,300,073 A | 4/1994 | Ray et al. |
| 5,306,275 A | 4/1994 | Bryan |
| 5,306,308 A | 4/1994 | Gross et al. |
| 5,306,309 A | 4/1994 | Wagner et al. |
| 5,326,364 A | 7/1994 | Clift, Jr. et al. |
| 5,330,479 A | 7/1994 | Whitmore |
| 5,360,431 A | 11/1994 | Puno et al. |
| 5,368,596 A | 11/1994 | Burkhart |
| 5,370,697 A | 12/1994 | Baumgartner |
| 5,372,598 A | 12/1994 | Luhr et al. |
| 5,400,784 A | 3/1995 | Durand et al. |
| 5,401,269 A | 3/1995 | Buttner-Janz et al. |
| 5,413,576 A | 5/1995 | Rivard |
| 5,415,661 A | 5/1995 | Holmes |
| 5,425,773 A | 6/1995 | Boyd et al. |
| 5,437,672 A | 8/1995 | Alleyne |
| 5,445,639 A | 8/1995 | Kuslich et al. |
| 5,458,642 A | 10/1995 | Beer et al. |
| 5,458,643 A | 10/1995 | Oka et al. |
| 5,462,542 A | 10/1995 | Alesi, Jr. |
| 5,487,756 A | 1/1996 | Kallesoe et al. |
| 5,491,882 A | 2/1996 | Walston et al. |
| 5,496,318 A | 3/1996 | Howland et al. |
| 5,507,823 A | 4/1996 | Walston et al. |
| 5,509,918 A | 4/1996 | Romano |
| 5,514,180 A | 5/1996 | Heggeness et al. |
| 5,527,312 A | 6/1996 | Ray |
| 5,527,314 A | 6/1996 | Brumfield et al. |
| 5,534,028 A | 7/1996 | Bao et al. |
| 5,534,030 A | 7/1996 | Navarro et al. |
| 5,540,706 A | 7/1996 | Aust et al. |
| 5,545,229 A | 8/1996 | Parsons et al. |
| 5,549,619 A | 8/1996 | Peters et al. |
| 5,556,431 A | 9/1996 | Buttner-Janz |
| 5,562,738 A | 10/1996 | Boyd et al. |
| 5,571,105 A | 11/1996 | Gundolf |
| 5,571,131 A | 11/1996 | Ek et al. |
| 5,571,189 A | 11/1996 | Kuslich |
| 5,571,191 A | 11/1996 | Fitz |
| 5,577,995 A | 11/1996 | Walker et al. |
| 5,586,989 A | 12/1996 | Bray, Jr. |
| 5,591,165 A | 1/1997 | Jackson |
| 5,603,713 A | 2/1997 | Aust et al. |
| 5,638,700 A | 6/1997 | Shechter |
| 5,645,597 A | 7/1997 | Krapiva |
| 5,645,599 A | 7/1997 | Samani |
| 5,649,947 A | 7/1997 | Auerbach et al. |
| 5,653,762 A | 8/1997 | Pisharodi |
| 5,674,295 A | 10/1997 | Ray et al. |
| 5,674,296 A | 10/1997 | Bryan et al. |
| 5,676,701 A | 10/1997 | Yuan et al. |
| 5,683,464 A | 11/1997 | Wagner et al. |
| 5,683,466 A | 11/1997 | Vitale |
| 5,700,265 A | 12/1997 | Romano |
| 5,702,450 A | 12/1997 | Bisserie |
| 5,707,373 A | 1/1998 | Sevrain et al. |
| 5,713,542 A | 2/1998 | Benoit |
| 5,716,415 A | 2/1998 | Steffee |
| 5,725,582 A | 3/1998 | Bevan et al. |
| 5,741,260 A | 4/1998 | Songer et al. |
| 5,741,261 A | 4/1998 | Moskovitz et al. |
| D395,138 S | 6/1998 | Ohata |
| 5,766,251 A | 6/1998 | Koshino |
| 5,766,253 A | 6/1998 | Brosnahan |
| 5,772,663 A | 6/1998 | Whiteside et al. |
| 5,797,916 A | 8/1998 | McDowell |
| 5,824,093 A | 10/1998 | Ray et al. |
| 5,824,094 A | 10/1998 | Serhan et al. |
| 5,836,948 A | 11/1998 | Zucherman et al. |
| 5,851,208 A | 12/1998 | Trott |
| 5,860,977 A | 1/1999 | Zucherman et al. |
| 5,865,846 A | 2/1999 | Bryan et al. |
| 5,868,745 A | 2/1999 | Alleyne |
| 5,876,404 A | 3/1999 | Zucherman et al. |
| 5,879,396 A | 3/1999 | Walston et al. |
| 5,888,203 A | 3/1999 | Goldberg |
| 5,893,889 A | 4/1999 | Harrington |
| 5,895,428 A | 4/1999 | Berry |
| RE36,221 E | 6/1999 | Breard et al. |
| 5,918,604 A | 7/1999 | Whelan |
| 5,951,555 A | 9/1999 | Rehak et al. |
| 5,964,765 A | 10/1999 | Fenton et al. |
| 5,993,452 A | 11/1999 | Vandewalle |
| 5,997,542 A | 12/1999 | Burke |
| 6,001,130 A | 12/1999 | Bryan et al. |
| 6,014,588 A | 1/2000 | Fitz |
| 6,019,763 A | 2/2000 | Nakamura et al. |
| 6,019,792 A | 2/2000 | Cauthen |
| 6,039,763 A | 3/2000 | Shelokov |
| 6,048,342 A | 4/2000 | Zucherman et al. |
| 6,050,998 A | 4/2000 | Fletcher |
| 6,063,121 A | 5/2000 | Xavier et al. |

(56) References Cited

U.S. PATENT DOCUMENTS

| | | |
|---|---|---|
| 6,066,325 A | 5/2000 | Wallace et al. |
| 6,068,630 A | 5/2000 | Zucherman et al. |
| RE36,758 E | 6/2000 | Fitz |
| 6,080,157 A | 6/2000 | Cathro et al. |
| 6,099,531 A | 8/2000 | Bonutti |
| 6,102,347 A | 8/2000 | Benoit |
| 6,106,558 A | 8/2000 | Picha |
| 6,113,637 A | 9/2000 | Gill et al. |
| 6,132,464 A | 10/2000 | Martin |
| 6,132,465 A | 10/2000 | Ray et al. |
| 6,146,422 A | 11/2000 | Lawson |
| 6,156,067 A | 12/2000 | Bryan et al. |
| 6,179,839 B1 | 1/2001 | Weiss et al. |
| D439,340 S | 3/2001 | Michelson |
| 6,200,322 B1 | 3/2001 | Branch et al. |
| 6,293,949 B1 | 9/2001 | Justis et al. |
| D450,122 S | 11/2001 | Michelson |
| 6,325,803 B1 | 12/2001 | Schumacher et al. |
| D454,953 S | 3/2002 | Michelson |
| 6,368,325 B1 | 4/2002 | McKinley et al. |
| 6,368,350 B1 | 4/2002 | Erickson et al. |
| 6,371,958 B1 | 4/2002 | Overaker |
| 6,375,573 B2 | 4/2002 | Romano |
| 6,379,386 B1 | 4/2002 | Resch et al. |
| D460,188 S | 7/2002 | Michelson |
| D460,189 S | 7/2002 | Michelson |
| 6,419,678 B1 | 7/2002 | Asfora |
| 6,419,703 B1 | 7/2002 | Fallin et al. |
| 6,436,099 B1 | 8/2002 | Drewry et al. |
| 6,436,101 B1 | 8/2002 | Hamada et al. |
| 6,436,146 B1 | 8/2002 | Hassler et al. |
| D463,560 S | 9/2002 | Michelson |
| 6,447,544 B1 | 9/2002 | Michelson |
| 6,470,207 B1 | 10/2002 | Simon et al. |
| 6,565,605 B2 | 5/2003 | Goble et al. |
| 6,572,617 B1 | 6/2003 | Senegas |
| 6,579,318 B2 | 6/2003 | Varga et al. |
| 6,579,319 B2 | 6/2003 | Goble et al. |
| 6,589,244 B1 | 7/2003 | Sevrain et al. |
| 6,600,956 B2 | 7/2003 | Maschino et al. |
| 6,607,530 B1 | 8/2003 | Carl et al. |
| 6,610,091 B1 | 8/2003 | Reiley |
| D479,331 S | 9/2003 | Pike et al. |
| 6,626,944 B1 | 9/2003 | Taylor |
| 6,641,614 B1 | 11/2003 | Wagner et al. |
| 6,656,195 B2 | 12/2003 | Peters et al. |
| 6,669,697 B1 | 12/2003 | Pisharodi |
| 6,669,729 B2 | 12/2003 | Chin |
| 6,706,068 B2 | 3/2004 | Ferree |
| 6,743,232 B2 | 6/2004 | Overaker et al. |
| 6,761,720 B1 | 7/2004 | Senegas |
| 6,764,491 B2 | 7/2004 | Frey et al. |
| 6,770,095 B2 | 8/2004 | Grinberg et al. |
| 6,783,527 B2 | 8/2004 | Drewry et al. |
| 6,790,210 B1 | 9/2004 | Cragg et al. |
| 6,802,863 B2 | 10/2004 | Lawson et al. |
| 6,811,567 B2 | 11/2004 | Reiley |
| 6,902,566 B2 | 6/2005 | Zucherman et al. |
| 6,908,484 B2 | 6/2005 | Zubok et al. |
| 6,966,930 B2 | 11/2005 | Arnin et al. |
| 6,974,478 B2 | 12/2005 | Reiley et al. |
| 6,974,479 B2 | 12/2005 | Trieu |
| D517,404 S | 3/2006 | Schluter |
| 7,008,429 B2 | 3/2006 | Golobek |
| 7,013,675 B2 | 3/2006 | Marquez-Pickering |
| 7,051,451 B2 | 5/2006 | Augostino et al. |
| 7,074,238 B2 | 7/2006 | Stinson et al. |
| 7,101,375 B2 | 9/2006 | Zucherman et al. |
| 7,223,269 B2 | 5/2007 | Chappuis |
| D565,180 S | 3/2008 | Liao |
| 7,371,238 B2 | 5/2008 | Sololeski et al. |
| 7,458,981 B2 | 12/2008 | Fielding et al. |
| 7,517,358 B2 | 4/2009 | Petersen |
| 7,537,611 B2 | 5/2009 | Lee |
| 7,559,940 B2 | 7/2009 | McGuire et al. |
| 7,563,286 B2 | 7/2009 | Gerber et al. |
| 7,585,300 B2 | 9/2009 | Cha |
| 7,608,104 B2 | 10/2009 | Yuan et al. |
| 7,695,472 B2 | 4/2010 | Young |
| 7,799,077 B2 | 9/2010 | Lang et al. |
| 7,806,895 B2 | 10/2010 | Weier et al. |
| 7,846,183 B2 | 12/2010 | Blain |
| 7,862,590 B2 | 1/2011 | Lim et al. |
| 7,935,136 B2 | 5/2011 | Alamin et al. |
| D643,121 S | 8/2011 | Milford et al. |
| 7,993,370 B2 | 8/2011 | Jahng |
| 7,998,172 B2 | 8/2011 | Blain |
| 8,052,728 B2 | 11/2011 | Hestad |
| 8,109,971 B2 | 2/2012 | Hale |
| 8,133,225 B2 | 3/2012 | Pieske |
| 8,163,016 B2 | 4/2012 | Linares |
| 8,177,810 B2 | 5/2012 | Ferree |
| 8,192,468 B2 | 6/2012 | Biedermann et al. |
| 8,216,275 B2 | 7/2012 | Fielding et al. |
| 8,231,661 B2 | 7/2012 | Carls |
| 8,246,655 B2 | 8/2012 | Jackson et al. |
| 8,267,966 B2 | 9/2012 | McCormack et al. |
| 8,292,954 B2 | 10/2012 | Robinson et al. |
| 8,306,307 B2 | 11/2012 | Koike et al. |
| 8,382,801 B2 | 2/2013 | Lamborne et al. |
| 8,394,125 B2 | 3/2013 | Assell |
| 8,460,346 B2 | 6/2013 | Ralph et al. |
| 8,486,078 B2 | 7/2013 | Carl et al. |
| 8,496,691 B2 | 7/2013 | Blain |
| 8,579,903 B2 | 11/2013 | Carl |
| 8,652,137 B2 | 2/2014 | Blain et al. |
| 8,740,942 B2 | 6/2014 | Blain |
| 8,740,949 B2 | 6/2014 | Blain |
| 8,753,345 B2 | 6/2014 | McCormack et al. |
| 8,784,423 B2 | 7/2014 | Kowarsch et al. |
| 8,858,597 B2 | 10/2014 | Blain |
| 8,882,804 B2 | 11/2014 | Blain |
| 8,961,613 B2 | 2/2015 | Assell et al. |
| D724,733 S | 3/2015 | Blain et al. |
| 8,974,456 B2 | 3/2015 | Allen et al. |
| 8,979,529 B2 | 3/2015 | Marcus |
| 8,992,533 B2 | 3/2015 | Blain et al. |
| 8,998,953 B2 | 4/2015 | Blain |
| 9,017,389 B2 | 4/2015 | Assell et al. |
| 9,060,787 B2 | 6/2015 | Blain et al. |
| 9,101,410 B1 | 8/2015 | Urrea |
| D739,935 S | 9/2015 | Blain et al. |
| 9,149,283 B2 | 10/2015 | Assell et al. |
| 9,161,763 B2 | 10/2015 | Assell et al. |
| 9,179,943 B2 | 11/2015 | Blain |
| 9,220,547 B2 | 12/2015 | Blain et al. |
| D748,262 S | 1/2016 | Blain |
| 9,233,006 B2 | 1/2016 | Assell et al. |
| D748,793 S | 2/2016 | Blain |
| 9,265,546 B2 | 2/2016 | Blain |
| 9,271,765 B2 | 3/2016 | Blain |
| 9,301,786 B2 | 4/2016 | Blain |
| 9,314,277 B2 | 4/2016 | Assell et al. |
| 9,345,488 B2 | 5/2016 | Assell et al. |
| 9,421,044 B2 | 8/2016 | Blain et al. |
| D765,853 S | 9/2016 | Blain et al. |
| D765,854 S | 9/2016 | Blain et al. |
| 9,456,855 B2 | 10/2016 | Blain et al. |
| 9,517,077 B2 | 12/2016 | Blain et al. |
| D777,921 S | 1/2017 | Blain et al. |
| D780,315 S | 2/2017 | Blain et al. |
| 9,572,602 B2 | 2/2017 | Blain et al. |
| D790,062 S | 6/2017 | Blain et al. |
| 9,675,387 B2 | 6/2017 | Blain |
| 9,743,937 B2 | 8/2017 | Blain et al. |
| 9,808,294 B2 | 11/2017 | Blain |
| 9,820,784 B2 | 11/2017 | Blain et al. |
| 9,839,450 B2 | 12/2017 | Blain et al. |
| D810,942 S | 2/2018 | Blain et al. |
| D812,754 S | 3/2018 | Blain et al. |
| 9,936,984 B2 | 4/2018 | Blain |
| 10,022,161 B2 | 7/2018 | Blain |
| 10,085,776 B2 | 10/2018 | Blain |
| D834,194 S | 11/2018 | Blain et al. |

(56) References Cited

U.S. PATENT DOCUMENTS

| | | |
|---|---|---|
| 10,194,955 B2 | 2/2019 | Blain et al. |
| 10,251,679 B2 | 4/2019 | Blain et al. |
| 2001/0018614 A1 | 8/2001 | Bianchi |
| 2002/0018799 A1 | 2/2002 | Spector et al. |
| 2002/0019637 A1 | 2/2002 | Frey et al. |
| 2002/0029039 A1 | 3/2002 | Zucherman et al. |
| 2002/0040227 A1 | 4/2002 | Harari |
| 2002/0065557 A1 | 5/2002 | Goble et al. |
| 2002/0072800 A1 | 6/2002 | Goble et al. |
| 2002/0077700 A1 | 6/2002 | Varga et al. |
| 2002/0086047 A1 | 7/2002 | Mueller et al. |
| 2002/0120335 A1 | 8/2002 | Angelucci et al. |
| 2002/0123806 A1 | 9/2002 | Reiley |
| 2002/0151895 A1 | 10/2002 | Soboleski et al. |
| 2002/0173800 A1 | 11/2002 | Dreyfuss et al. |
| 2002/0173813 A1 | 11/2002 | Peterson et al. |
| 2002/0198527 A1 | 12/2002 | Muckter |
| 2003/0004572 A1 | 1/2003 | Goble et al. |
| 2003/0028250 A1 | 2/2003 | Reiley et al. |
| 2003/0040797 A1 | 2/2003 | Fallin et al. |
| 2003/0120343 A1 | 6/2003 | Whelan |
| 2003/0176919 A1 | 9/2003 | Schmieding |
| 2003/0176922 A1 | 9/2003 | Lawson et al. |
| 2003/0187454 A1 | 10/2003 | Gill et al. |
| 2003/0191532 A1 | 10/2003 | Goble et al. |
| 2003/0204259 A1 | 10/2003 | Goble et al. |
| 2003/0216669 A1 | 11/2003 | Lang et al. |
| 2003/0233146 A1 | 12/2003 | Grinberg et al. |
| 2004/0006391 A1 | 1/2004 | Reiley |
| 2004/0010318 A1 | 1/2004 | Ferree |
| 2004/0024462 A1 | 2/2004 | Ferree et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0059429 A1 | 3/2004 | Amin et al. |
| 2004/0087954 A1 | 5/2004 | Allen et al. |
| 2004/0116927 A1 | 6/2004 | Graf |
| 2004/0127989 A1 | 7/2004 | Dooris et al. |
| 2004/0143264 A1 | 7/2004 | McAfee |
| 2004/0176844 A1 | 9/2004 | Zubok et al. |
| 2004/0199166 A1 | 10/2004 | Schmieding et al. |
| 2004/0215341 A1 | 10/2004 | Sybert et al. |
| 2004/0230201 A1 | 11/2004 | Yuan et al. |
| 2004/0230304 A1 | 11/2004 | Yuan et al. |
| 2005/0010291 A1 | 1/2005 | Stinson et al. |
| 2005/0015146 A1 | 1/2005 | Louis et al. |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0059972 A1 | 3/2005 | Biscup |
| 2005/0131409 A1 | 6/2005 | Chervitz et al. |
| 2005/0131538 A1 | 6/2005 | Chervitz et al. |
| 2005/0143818 A1 | 6/2005 | Yuan et al. |
| 2005/0159746 A1 | 7/2005 | Grab et al. |
| 2005/0177240 A1 | 8/2005 | Blain |
| 2005/0197700 A1 | 9/2005 | Boehem et al. |
| 2005/0216017 A1 | 9/2005 | Fielding et al. |
| 2005/0240201 A1 | 10/2005 | Yeung |
| 2005/0251256 A1 | 11/2005 | Reiley |
| 2005/0256494 A1 | 11/2005 | Datta |
| 2006/0004367 A1 | 1/2006 | Alamin et al. |
| 2006/0036323 A1 | 2/2006 | Carl et al. |
| 2006/0041311 A1 | 2/2006 | McLeer |
| 2006/0084985 A1 | 4/2006 | Kim |
| 2006/0085006 A1 | 4/2006 | Ek et al. |
| 2006/0085072 A1 | 4/2006 | Funk et al. |
| 2006/0111782 A1 | 5/2006 | Petersen |
| 2006/0116684 A1 | 6/2006 | Whelan |
| 2006/0149375 A1 | 7/2006 | Yuan et al. |
| 2006/0200137 A1 | 9/2006 | Soboleski et al. |
| 2006/0241601 A1 | 10/2006 | Trautwein et al. |
| 2006/0241758 A1 | 10/2006 | Peterman et al. |
| 2006/0293691 A1 | 12/2006 | Mitra et al. |
| 2007/0055236 A1 | 3/2007 | Hudgins et al. |
| 2007/0055252 A1 | 3/2007 | Blain et al. |
| 2007/0055373 A1 | 3/2007 | Hudgins et al. |
| 2007/0078464 A1 | 4/2007 | Jones et al. |
| 2007/0100452 A1 | 5/2007 | Prosser |
| 2007/0118218 A1 | 5/2007 | Hooper |
| 2007/0123863 A1 | 5/2007 | Winslow et al. |
| 2007/0135814 A1 | 6/2007 | Farris |
| 2007/0149976 A1 | 6/2007 | Hale et al. |
| 2007/0179619 A1 | 8/2007 | Grab |
| 2007/0250166 A1 | 10/2007 | McKay |
| 2007/0270812 A1 | 11/2007 | Peckham |
| 2008/0009866 A1 | 1/2008 | Alamin et al. |
| 2008/0058929 A1 | 3/2008 | Whelan |
| 2008/0177264 A1 | 7/2008 | Alamin et al. |
| 2008/0177326 A1 | 7/2008 | Thompson |
| 2008/0183211 A1 | 7/2008 | Lamborne et al. |
| 2008/0228225 A1 | 9/2008 | Trautwein et al. |
| 2008/0262549 A1 | 10/2008 | Bennett et al. |
| 2008/0287996 A1 | 11/2008 | Soholeski et al. |
| 2009/0005818 A1 | 1/2009 | Chin et al. |
| 2009/0005873 A1 | 1/2009 | Slivka et al. |
| 2009/0018662 A1 | 1/2009 | Pasquet et al. |
| 2009/0024166 A1 | 1/2009 | Carl et al. |
| 2009/0076617 A1 | 3/2009 | Ralph et al. |
| 2009/0105766 A1 | 4/2009 | Thompson et al. |
| 2009/0125066 A1 | 5/2009 | Kraus et al. |
| 2009/0138048 A1 | 5/2009 | Baccelli et al. |
| 2009/0171360 A1 | 7/2009 | Whelan |
| 2009/0198282 A1 | 8/2009 | Fielding et al. |
| 2009/0264928 A1 | 10/2009 | Blain |
| 2009/0264929 A1 | 10/2009 | Alamin et al. |
| 2009/0270918 A1 | 10/2009 | Attia et al. |
| 2009/0270929 A1 | 10/2009 | Suddaby |
| 2009/0306716 A1* | 12/2009 | Beger ............... A61B 17/7062 606/249 |
| 2009/0326589 A1 | 12/2009 | Lemoine et al. |
| 2010/0010548 A1* | 1/2010 | Hermida Ochoa .................... A61B 17/06066 606/86 A |
| 2010/0076503 A1 | 3/2010 | Beyar et al. |
| 2010/0131008 A1 | 5/2010 | Overes et al. |
| 2010/0179553 A1 | 7/2010 | Ralph et al. |
| 2010/0185241 A1 | 7/2010 | Malandain et al. |
| 2010/0191286 A1 | 7/2010 | Butler |
| 2010/0204700 A1 | 8/2010 | Falahee |
| 2010/0204732 A1* | 8/2010 | Aschmann ......... A61B 17/7053 606/249 |
| 2010/0234894 A1 | 9/2010 | Alamin et al. |
| 2010/0274289 A1* | 10/2010 | Carls ................... A61B 17/842 606/263 |
| 2010/0298829 A1* | 11/2010 | Schaller ............... A61B 17/82 606/74 |
| 2010/0318133 A1 | 12/2010 | Tornier |
| 2011/0022050 A1 | 1/2011 | McClellan et al. |
| 2011/0022089 A1 | 1/2011 | Assell et al. |
| 2011/0040301 A1 | 2/2011 | Blain et al. |
| 2011/0082503 A1 | 4/2011 | Blain |
| 2011/0098816 A1 | 4/2011 | Jacob et al. |
| 2011/0160772 A1* | 6/2011 | Arcenio ............. A61B 17/7053 606/248 |
| 2011/0172712 A1 | 7/2011 | Chee et al. |
| 2011/0245875 A1 | 10/2011 | Karim |
| 2011/0295318 A1 | 12/2011 | Alamin et al. |
| 2011/0313456 A1 | 12/2011 | Blain |
| 2012/0035658 A1 | 2/2012 | Goble et al. |
| 2012/0041441 A1 | 2/2012 | Bernstein et al. |
| 2012/0046749 A1 | 2/2012 | Tatsumi |
| 2012/0101502 A1* | 4/2012 | Kartalian ............. A61B 17/68 606/74 |
| 2012/0150231 A1 | 6/2012 | Alamin et al. |
| 2012/0221048 A1 | 8/2012 | Blain |
| 2012/0221049 A1 | 8/2012 | Blain |

(56) References Cited

U.S. PATENT DOCUMENTS

| | | |
|---|---|---|
| 2012/0221060 A1 | 8/2012 | Blain |
| 2012/0245586 A1 | 9/2012 | Lehenkari et al. |
| 2012/0271354 A1 | 10/2012 | Baccelli et al. |
| 2012/0277801 A1 | 11/2012 | Marik et al. |
| 2012/0310244 A1 | 12/2012 | Blain et al. |
| 2013/0023878 A1 | 1/2013 | Belliard et al. |
| 2013/0041410 A1 | 2/2013 | Hestad et al. |
| 2013/0079778 A1 | 3/2013 | Azuero et al. |
| 2013/0123923 A1 | 5/2013 | Pavlov et al. |
| 2013/0245693 A1 | 9/2013 | Blain |
| 2013/0253649 A1 | 9/2013 | Davis |
| 2013/0261625 A1 | 10/2013 | Koch et al. |
| 2013/0325065 A1 | 12/2013 | Malandain et al. |
| 2014/0012318 A1 | 1/2014 | Goel |
| 2014/0066758 A1 | 3/2014 | Marik et al. |
| 2014/0228883 A1 | 8/2014 | Blain |
| 2014/0257397 A1 | 9/2014 | Akbarnia et al. |
| 2014/0277148 A1 | 9/2014 | Blain et al. |
| 2014/0277149 A1 | 9/2014 | Rooney et al. |
| 2014/0336653 A1 | 11/2014 | Bromer |
| 2014/0378976 A1 | 12/2014 | Garcia |
| 2015/0081023 A1 | 3/2015 | Blain |
| 2015/0094766 A1 | 4/2015 | Blain et al. |
| 2015/0094767 A1 | 4/2015 | Blain et al. |
| 2015/0119988 A1 | 4/2015 | Assell et al. |
| 2015/0164516 A1 | 6/2015 | Blain et al. |
| 2015/0164652 A1 | 6/2015 | Assell et al. |
| 2015/0190149 A1 | 7/2015 | Assell et al. |
| 2015/0196330 A1 | 7/2015 | Blain |
| 2015/0209096 A1 | 7/2015 | Gephart |
| 2015/0257770 A1 | 9/2015 | Assell et al. |
| 2015/0257773 A1 | 9/2015 | Blain et al. |
| 2015/0327872 A1 | 11/2015 | Assell et al. |
| 2015/0342648 A1 | 12/2015 | McCormack et al. |
| 2016/0051294 A1 | 2/2016 | Blain |
| 2016/0113692 A1 | 4/2016 | Knoepfle |
| 2016/0128739 A1 | 5/2016 | Blain et al. |
| 2016/0128838 A1 | 5/2016 | Assell et al. |
| 2016/0213481 A1 | 7/2016 | Blain |
| 2016/0324549 A1 | 11/2016 | Blain |
| 2017/0000527 A1 | 1/2017 | Blain et al. |
| 2017/0105767 A1 | 4/2017 | Blain |
| 2017/0239060 A1 | 8/2017 | Blain |
| 2017/0281232 A1 | 10/2017 | Smith |
| 2018/0049780 A1 | 2/2018 | Blain |
| 2018/0085148 A1 | 3/2018 | Blain |
| 2019/0142478 A1 | 5/2019 | Blain |

FOREIGN PATENT DOCUMENTS

| | | |
|---|---|---|
| DE | 201 12 123 | 9/2001 |
| DE | 101 35 771 | 2/2003 |
| EP | 0 238 219 | 9/1987 |
| EP | 0 322 334 | 6/1989 |
| EP | 0 392 124 | 10/1990 |
| EP | 0 610 837 | 8/1994 |
| EP | 0 928 603 | 7/1999 |
| EP | 1 201 202 | 5/2002 |
| EP | 1 201 256 | 5/2002 |
| EP | 2 138 122 | 12/2009 |
| EP | 2 822 482 | 1/2015 |
| EP | 2 919 717 | 9/2015 |
| FR | 2 704 745 | 11/1994 |
| FR | 2 722 980 | 2/1996 |
| GB | 2 366 736 | 3/2002 |
| JP | 53-005889 | 1/1978 |
| JP | 62-270147 | 11/1987 |
| JP | 03-100154 | 4/1991 |
| JP | 03-240660 | 10/1991 |
| JP | 08-509918 | 10/1996 |
| JP | 10-179622 | 7/1998 |
| JP | 2000-201941 | 7/2000 |
| JP | 2000-210297 | 8/2000 |
| JP | 2003-079649 | 3/2003 |
| JP | 2004-508888 | 3/2004 |
| JP | 2004-181236 | 7/2004 |
| JP | 2006-230722 | 9/2006 |
| JP | 2006-528540 | 12/2006 |
| JP | 2007-503884 | 3/2007 |
| JP | 2007-517627 | 7/2007 |
| JP | 2007-190389 | 8/2007 |
| JP | 2008-510526 | 4/2008 |
| JP | 2009-533167 | 9/2009 |
| JP | 2010-173739 | 8/2010 |
| JP | 2012-509740 | 4/2012 |
| JP | 2012-521221 | 9/2012 |
| JP | 2013-534451 | 9/2013 |
| JP | 2014-513583 | 6/2014 |
| MX | 6012309 | 1/2007 |
| WO | WO 93/014721 | 8/1993 |
| WO | WO 94/004088 | 3/1994 |
| WO | WO 97/047246 | 12/1997 |
| WO | WO 98/048717 | 11/1998 |
| WO | WO 99/023963 | 5/1999 |
| WO | WO 00/038582 | 7/2000 |
| WO | WO 00/053126 | 9/2000 |
| WO | WO 01/030248 | 5/2001 |
| WO | WO 02/045765 | 6/2002 |
| WO | WO 02/065954 | 8/2002 |
| WO | WO 02/096300 | 12/2002 |
| WO | WO 03/101350 | 12/2003 |
| WO | WO 2004/071358 | 8/2004 |
| WO | WO 2005/020850 | 3/2005 |
| WO | WO 2005/072661 | 8/2005 |
| WO | WO 2006/023980 | 3/2006 |
| WO | WO 2006/096803 | 9/2006 |
| WO | WO 2008/008522 | 1/2008 |
| WO | WO 2009/013397 | 1/2009 |
| WO | WO 2009/021876 | 2/2009 |
| WO | WO 2010/060072 | 5/2010 |
| WO | WO 2010/122472 | 10/2010 |
| WO | WO 2011/011621 | 1/2011 |
| WO | WO 2012/007941 | 1/2012 |
| WO | WO 2012/116266 | 8/2012 |
| WO | WO 2013/022880 | 2/2013 |
| WO | WO 2013/138655 | 9/2013 |
| WO | WO 2014/078541 | 5/2014 |
| WO | WO 2014/158690 | 10/2014 |
| WO | WO 2016/044432 | 3/2016 |

OTHER PUBLICATIONS

ArthroTek, "CurvTek® Bone Tunneling System," Surgical Technique, 2000, pp. 6.

ArthroTek, "CurvTek® Bone Tunneling System," User's Manual, 2000, pp. 20.

Ash, H.E., "Proximal Interphalangeal Joint Dimensions for the Design of a Surface Replacement Prosthesis", School of Engineering, University of Durham, Proceedings of the Institution of Mechanical Engineers Part H Journal of Engineering in Medicine Feb. 1996, vol. 210, No. 2, pp. 95-108.

Beaman, MD et al., "Substance P Innervation of Lumbar Spine Facet Joints", Spine, 1993, vol. 18, No. 8, pp. 1044-1049.

Butterman, et al., "An Experimental Method for Measuring Force on the Spinal Facet Joint: Description and Application of the Method", Journal of Biomechanical Engineering, Nov. 1991, vol. 113, pp. 375-386.

Cruess et al., "The Response of Articular Cartilage to Weight-Bearing Against Metal", The Journal of Bone and Joint Surgery, Aug. 1984, vol. 66-B, No. 4, pp. 592-597.

Dalldorf et al., "Rate of Degeneration of Human Acetabular Cartilage after Hemiarthroplasty", The Journal of Bone and Joint Surgery, Jun. 1995, vol. 77. No. 6, pp. 877-882.

E-mail from 3rd Party citing U.S. Appl. No. 60/721,909; U.S. Appl. No. 60/750,005 and U.S. Appl. No. 60/749,000, initial e-mail dated May 11, 2009, reply e-mail dated May 18, 2009.

Frost, Harold M., "From Wolff's Law to the Utah Paradigm: Insights About Bone Physiology and Its Clinical Applications", The Anatomical Record, 2001, vol. 262, pp. 398-419.

King et al., "Mechanism of Spinal Injury Due to Caudocephalad Acceleration," Symposium on the Lumbar Spine, Orthopedic Clinic of North America, Jan. 1975, vol. 6, pp. 19-31.

(56) References Cited

OTHER PUBLICATIONS

Kurtz, PhD et al., "Isoelastic Polyaryletheretherketone Implants for Total Joint Replacement", Peek Biomaterials Handbook, Ch. 14, 2012, pp. 221-226.
Meisel et al., "Minimally Invasive Facet Restoration Implant for Chronic Lumbar Zygapophysial Pain: 1-Year Outcomes", Annals of Surgical Innovation and Research (ASIR), 2014, vol. 8, No. 7, pp. 6.
Panjabi, PhD et al., "Articular Facets of the Human Spine: Quantitative Three-Dimensional Anatomy", Spine, 1993, vol. 18, No. 10, pp. 1298-1310.
Parteq Innovations, "Facet Joint Implants & Resurfacing Devices," Technology Opportunity Bulletin, Tech ID 1999-012, Queen's University, Ontario Canada, pp. 2.
Ravikumar et al., "Internal Fixation Versus Hemiarthroplasty Versus Total Hip Arthroplasty for Displaced Subcapital Fractures of Femur— 13 year Results of a Prospective Randomised Study", International Journal of the Care of the Injured (Injury), 2000, vol. 31, pp. 793-797.
Schendel et al., "Experimental Measurement of Ligament Force, Facet Force, and Segment Motion in the Human Lumbar Spine", Journal of Biomechanics, 1993, vol. 26, No. 4/5, pp. 427-438.
Tanno et al., "Which Portion in a Facet is Specifically Affected by Articular Cartilage Degeneration with Aging in the Human Lumbar Zygapophysial Joint?", Okajimas Folia Anatomica Japonica, May 2003, vol. 80, No. 1, pp. 29-34.
Official Communication in Australian Application No. 2005213459, dated Dec. 11, 2009.
Official Communication in Australian Application No. 2005213459, dated Dec. 15, 2010.
Official Communication in Australian Application No. 2011226832, dated Sep. 4, 2012.
Official Communication in Australian Application No. 2011226832, dated Oct. 31, 2012.
Official Communication in Australian Application No. AU2013237744, dated Sep. 2, 2014.
Notice of Acceptance in Australian Application No. AU2013237744, dated Apr. 23, 2015.
Official Communication in Australian Application No. AU2015205875, dated Apr. 2, 2016.
Official Communication in Australian Application No. AU2015205875, dated Jun. 15, 2016.
Official Communication in Canadian Application No. 2,555,355, dated Sep. 2, 2011.
Official Communication in Canadian Application No. 2,803,783, dated Sep. 29, 2014.
Official Communication in Canadian Application No. 2,803,783, dated Aug. 5, 2015.
Official Communication in Canadian Application No. 2,803,783, dated Jul. 7, 2016.
Official Communication in European Application No. 05712981.9, dated Jul. 24, 2007.
Official Communication in European Application No. 05712981.9, dated Mar. 10, 2008.
Official Communication in European Application No. 05712981.9, dated Apr. 6, 2009.
Official Communication in European Application No. 05712981.9, dated Jun. 15, 2010.
Official Communication in European Application No. 10178979.0, dated Mar. 14, 2011.
Official Communication in European Application No. 10178979.0, dated Nov. 13, 2012.
Official Communication in European Application No. 10178979.0, dated Aug. 5, 2013.
Official Communication in European Application No. 14175088.5, dated Sep. 8, 2014.
Official Communication in European Application No. 14175088.5, dated Nov. 18, 2015.
Official Communication in Japanese Application No. 2006-552309, dated May 25, 2010.
Official Communication in Japanese Application No. 2006-552309, dated Feb. 15, 2011.
Official Communication in Japanese Application No. 2010-221380, dated Feb. 15, 2011.
Official Communication in Japanese Application No. 2012-272106, dated Dec. 3, 2013.
Official Communication in Japanese Application No. 2012-272106, dated May 26, 2014.
Official Communication in Japanese Application No. 2012-272106, dated Feb. 23, 2015.
Official Communication in Japanese Application No. 2012-272106, dated Nov. 2, 2015.
International Search Report and Written Opinion in International Application No. PCT/US2005/003753, dated Dec. 5, 2006.
International Preliminary Report and Written Opinion in International App No. PCT/US2005/003753, dated Jan. 9, 2007.
Official Communication in European Application No. 08730413.5, dated Feb. 16, 2012.
Official Communication in European Application No. 14177951.2, dated Nov. 13, 2014.
International Search Report and Written Opinion in International Application No. PCT/US2008/054607, dated Jul. 10, 2008.
International Preliminary Report on Patentability in International Application No. PCT/US2008/054607, dated Sep. 3, 2009.
Official Communication in Australian Application No. 2011292297, dated Jul. 10, 2013.
Official Communication in Australian Application No. 2014277721, dated Sep. 8, 2016.
Official Communication in Australian Application No. 2014277721, dated Jan. 9, 2017.
Official Communication in European Application No. 11818586.7, dated Nov. 6, 2014.
Official Communication in European Application No. 11818586.7, dated Feb. 3, 2017.
Official Communication in Japanese Application No. 2013-524882, dated Mar. 2, 2015.
Official Communication in Japanese Application No. 2013-524882, dated Nov. 16, 2015.
Official Communication in Japanese Application No. 2015-242990, dated Dec. 12, 2016.
International Search Report and Written Opinion in International Application No. PCT/US2011/047432, dated Dec. 12, 2011.
International Preliminary Report on Patentability in International Application No. PCT/US2011/047432, dated Feb. 28, 2013.
Official Communication in Australian Application No. AU2012222229, dated Aug. 21, 2015.
Official Communication in Australian Application No. AU2012222229, dated May 11, 2016.
Official Communication in Australian Application No. AU2012222230, dated Aug. 21, 2015.
Official Communication in European Application No. EP12749447.4, dated Jan. 4, 2017.
Official Communication in European Application No. 12749251.0, dated Jan. 4, 2017.
Official Communication in Japanese Application No. JP 2013-555591, dated Jan. 4, 2016.
Official Communication in Japanese Application No. JP 2013-555592, dated Dec. 7, 2015.
Official Communication in Japanese Application No. JP 2013-555592, dated Aug. 8, 2016.
International Search Report in International Application No. PCT/US2012/026470, dated May 30, 2012.
International Preliminary Report on Patentability and Written Opinion in International Application No. PCT/US2012/026470, dated Sep. 6, 2013.
International Search Report and Written Opinion in International Application No. PCT/US2012/026472, dated Jun. 20, 2012.
International Preliminary Report on Patentability and Written Opinion in International Application No. PCT/US2012/026472, dated Mar. 12, 2014.
Official Communication in European Application No. 14774714.1, dated Oct. 21, 2016.

(56) References Cited

OTHER PUBLICATIONS

International Search Report and Written Opinion in International Application No. PCT/US2014/019302, dated May 18, 2015.
Official Communication in European Application No. 14776445.0, dated Nov. 7, 2016.
International Search Report and Written Opinion in International Application No. PCT/US2014/019325, dated Jun. 17, 2014.
International Preliminary Report on Patentability and Written Opinion in International Application No. PCT/US2014/019325, dated Sep. 24, 2015.
Official Communication in European Application No. 14850082.0, dated Aug. 31, 2016.
International Search Report and Written Opinion in International Application No. PCT/US2014/056598, dated Dec. 29, 2014.
International Preliminary Report on Patentability and Written Opinion in International Application No. PCT/US2014/056598, dated Apr. 7, 2016.
International Search Report and Written Opinion in International Application No. PCT/US2015/050441, dated Dec. 28, 2015.
International Preliminary Report on Patentability and Written Opinion in International Application No. PCT/US2015/050441, dated Mar. 30, 2017.
International Search Report and Written Opinion in International Application No. PCT/US2016/013062, dated Mar. 16, 2016.
International Search Report in International Application No. PCT/CA2002/000193 filed Feb. 15, 2002, dated Jun. 18, 2002.
International Search Report and Written Opinion in International Application No. PCT/US2004/028094, dated May 16, 2005.
International Preliminary Report on Patentability in International Application No. PCT/US2004/028094, dated Feb. 25, 2013.
International Search Report in International Application No. PCT/US2005/000987 filed Jan. 13, 2005, dated May 24, 2005.
International Preliminary Report on Patentability in International Application No. PCT/US2005/000987 filed Jan. 13, 2005, dated Jan. 17, 2006.
Official Communication in Australian Application No. AU2016231622, dated Nov. 22, 2018.
Official Communication in European Application No. 16180368.9, dated Jan. 11, 2018.
Official Communication in Canadian Application No. 2,804,223, dated Mar. 14, 2018.
Official Communication in European Application No. EP12749447.4, dated Nov. 14, 2018.
Official Communication in Japanese Application No. 2016-246368, dated Jul. 2, 2018.
Official Communication in Japanese Application No. JP 2013-555592, dated Jan. 5, 2018.
Official Communication in Japanese Application No. 2016-237460, dated Apr. 16, 2018.
Official Communication in Australian Application No. 2014241989, dated Jun. 20, 2018.
Official Communication in Australian Application No. 2014241989, dated Aug. 17, 2018.
Official Communication in Japanese Application No. JP 2016-500490, dated May 7, 2018.
Official Communication in Japanese Application No. JP 2016-500498, dated Jan. 5, 2018.
Official Communication in Japanese Application No. JP 2016-500498, dated Jul. 2, 2018.
Official Communication in Australian Application No. 2014327083, dated May 31, 2018.
Official Communication in Japanese Application No. JP 2016-517392, dated Jun. 4, 2018.
Official Communication in European Application No. 16743832.4, dated Jul. 24, 2018.
Sharpe Products, "Metal Round Disks", https://web.archive.org/web/20170705214756/https://sharpeproducts.com/store/metal-round-disks, as archived Jul. 5, 2017 in 3 pages.
Official Communication in Australian Application No. AU2016231622, dated Dec. 5, 2017.
Official Communication in Canadian Application No. 2,803,783, dated Apr. 5, 2017.
Official Communication in European Application No. 16180368.9, dated Mar. 31, 2017.
Official Communication in Canadian Application No. 2,804,223, dated Jun. 5, 2017.
Official Communication in Japanese Application No. 2015-242990, dated May 8, 2017.
Official Communication in Japanese Application No. 2015-242990, dated Aug. 21, 2017.
Official Communication in European Application No. EP12749447.4, dated Apr. 4, 2017.
Official Communication in European Application No. 12749251.0, dated May 9, 2017.
Official Communication in Japanese Application No. 2016-246368, dated Oct. 30, 2017.
Official Communication in Japanese Application No. 2016-237460, dated Oct. 23, 2017.
Official Communication in Australian Application No. 2014241989, dated Aug. 31, 2017.
Official Communication in Japanese Application No. JP 2016-500490, dated Nov. 27, 2017.
Official Communication in Australian Application No. 2014241994, dated Oct. 30, 2017.
International Preliminary Report on Patentability and Written Opinion in International Application No. PCT/US2016/013062, dated Aug. 10, 2017.
Notice of Acceptance in Australian Application No. AU2016231622, dated Dec. 4, 2018.
Official Communication in Japanese Application No. JP 2016-500498, dated Mar. 4, 2019.
Notice of Acceptance in Australian Application No. 2014327083, dated Apr. 3, 2019.
Official Communication in Japanese Application No. JP 2016-517392, dated Apr. 22, 2019.

\* cited by examiner

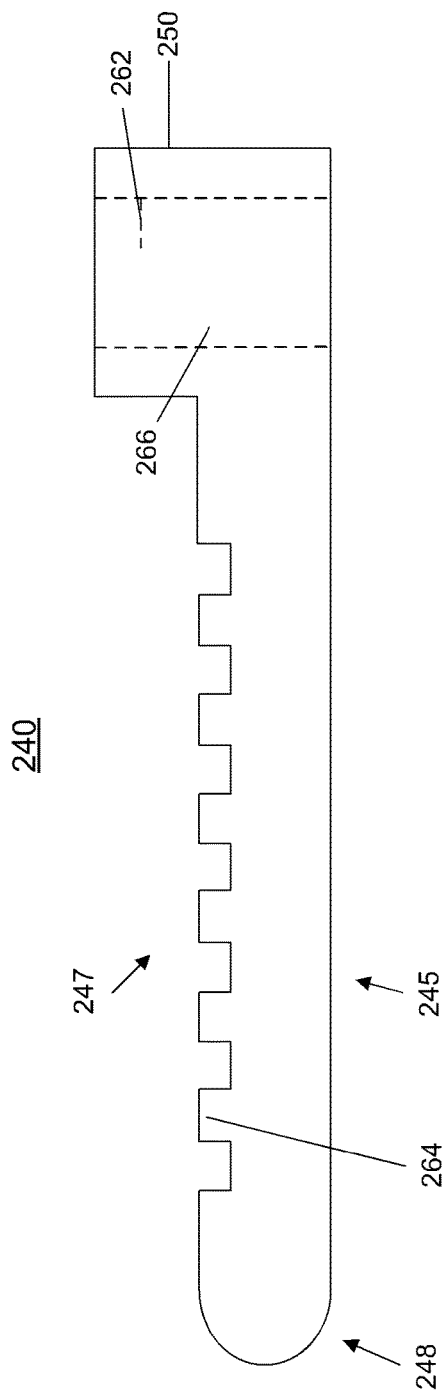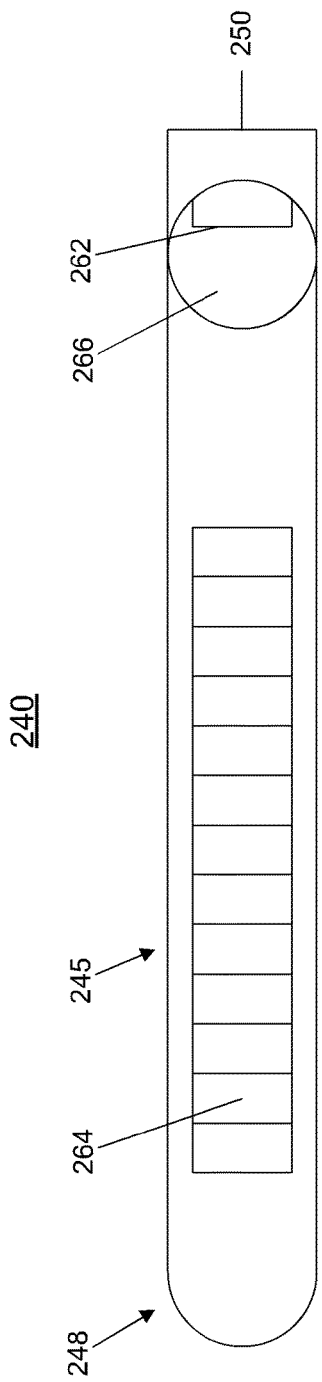

790

```
┌─────────────────────────────────────────────┐
│ Disposing a flexible band into contact with a first │
│ bone portion and a second bone portion.     │
│ 792                                         │
└─────────────────────────────────────────────┘
                      │
                      ▼
┌─────────────────────────────────────────────┐
│ Advancing a portion of the flexible band through an │
│ attachment connection until the first bone portion │
│ and the second bone portion are stabilized. │
│ 794                                         │
└─────────────────────────────────────────────┘
                      │
                      ▼
┌─────────────────────────────────────────────┐
│ Advancing a portion of a fastener through an │
│ aperture and into the first bone portion until the │
│ flexible band is secured to the first bone portion. │
│ 796                                         │
└─────────────────────────────────────────────┘
```

FIG. 16

APPARATUS FOR SPINAL FIXATION AND METHODS OF USE

CROSS-REFERENCE AND RELATED APPLICATIONS

This application is a divisional application of U.S. patent application Ser. No. 13/804,407, filed Mar. 14, 2013. This application is related to U.S. patent application Ser. No. 29/448,946 entitled "Flexible Elongate Member with a Portion to Receive a Bone Anchor," filed on Mar. 14, 2013.

BACKGROUND

Some embodiments described herein relate generally to methods and apparatus for stabilizing bone, for example, stabilizing vertebrae by securing the articular processes of the vertebrae.

Traumatic, inflammatory, and degenerative disorders of the spine can lead to severe pain and loss of mobility. One source of back and spine pain is related to degeneration of the facets of the spine or facet arthritis. Bony contact or grinding of degenerated facet joint surfaces can play a role in some pain syndromes. While many technological advances have focused on the intervertebral disc and artificial replacement or repair of the intervertebral disc, relatively little advancement in facet repair has been made. Facet joint and disc degeneration frequently occur together.

The current standard of care to address the degenerative problems with the facet joints is to fuse the two adjacent vertebrae. By performing this surgical procedure, the relative motion between the two adjacent vertebrae is stopped, thus stopping motion of the facets and any potential pain generated as a result thereof. Procedures to fuse two adjacent vertebrae often involve fixation and/or stabilization of the two adjacent vertebrae until the two adjacent vertebrae fuse.

Injuries and/or surgical procedure on and/or effecting other bones can also result in the desire to fixate and/or stabilize a bone until the bone, or bone portions, can fuse, for example, to stabilize a sternum after heart surgery, to stabilize a rib after a break, etc. Current procedures to fixate and/or stabilize adjacent vertebrae and/or other bones, however, can be slow and/or complex.

Accordingly, a need exists for an apparatus and methods to better stabilize and/or fixate a bone.

SUMMARY

In some embodiments, a method comprises forming a lumen in a first bone portion and forming a lumen in a second bone portion. The method further includes inserting a portion of a flexible fastening band through the lumen in the first bone portion and through the lumen in the second bone portion, and inserting the portion of the flexible fastening band into a fastener mechanism monolithically formed with the flexible fastening band. The method further includes advancing the portion of the flexible fastening band through the fastener mechanism until the first bone portion and the second bone portion are stabilized.

BRIEF DESCRIPTION OF THE DRAWINGS

FIGS. 8A and 8B are schematic illustrations of a flexible elongate body according to an embodiment.

FIG. 16 is a flowchart illustrating a method of stabilizing a bone portion according to an embodiment.

DETAILED DESCRIPTION

In some embodiments, a method comprises forming a lumen in a first bone portion and forming a lumen in a second bone portion. The method further includes inserting a portion of a flexible fastening band through the lumen in the first bone portion and through the lumen in the second bone portion, and inserting the portion of the flexible fastening band into a fastener mechanism monolithically formed with the flexible fastening band. The method further includes advancing the portion of the flexible fastening band through the fastener mechanism until the first bone portion and the second bone portion are stabilized.

In some embodiments, an apparatus includes a flexible elongate body and an anchor. The flexible elongate body includes a distal end portion, a body portion, and an attachment connection. The attachment connection receives the distal end portion of the flexible elongate body when the body portion is disposed in contact with a first bone portion and a second bone portion. The anchor receives a fastener configured to secure the flexible elongate body to the first bone portion via the anchor.

In some embodiments, a kit includes a flexible band and a fastener. The flexible band includes an interface portion configured to receive the fastener. The flexible band is configured to stabilize a first bone portion and a second bone portion. The fastener is configured to anchor the flexible band to the first bone portion such that the first bone portion, the second bone portion, and the flexible band are stabilized after being anchored.

As used in this specification, the singular forms "a," "an" and "the" include plural referents unless the context clearly dictates otherwise. Thus, for example, the term "a ratchet" is intended to mean a single ratchet or a combination of ratchets. As used in this specification, a substance can include any biologic and/or chemical substance, including, but not limited to, medicine, adhesives, etc. While exemplary references are made with respect to vertebra, in some embodiments another bone can be involved. While specific reference may be made to a specific vertebra, a subset of vertebrae, and/or a grouping of vertebrae, it is understood that any vertebra, subset, and/or grouping, or combination of vertebrae can be used.

The words "proximal" and "distal" generally refer to the direction closer to and away from, respectively, a center of a body. The embodiments described herein, however, can be arranged in any orientation relative to the center of the body. Thus, when discussing the embodiments described herein (specifically a flexible elongate body), the terms "proximal" and "distal" refer to a direction closer to and away from, respectively, an attachment connection or fastener mechanism, the position of which is visually presented with respect to specific embodiments in the attached figures.

Figure 1:
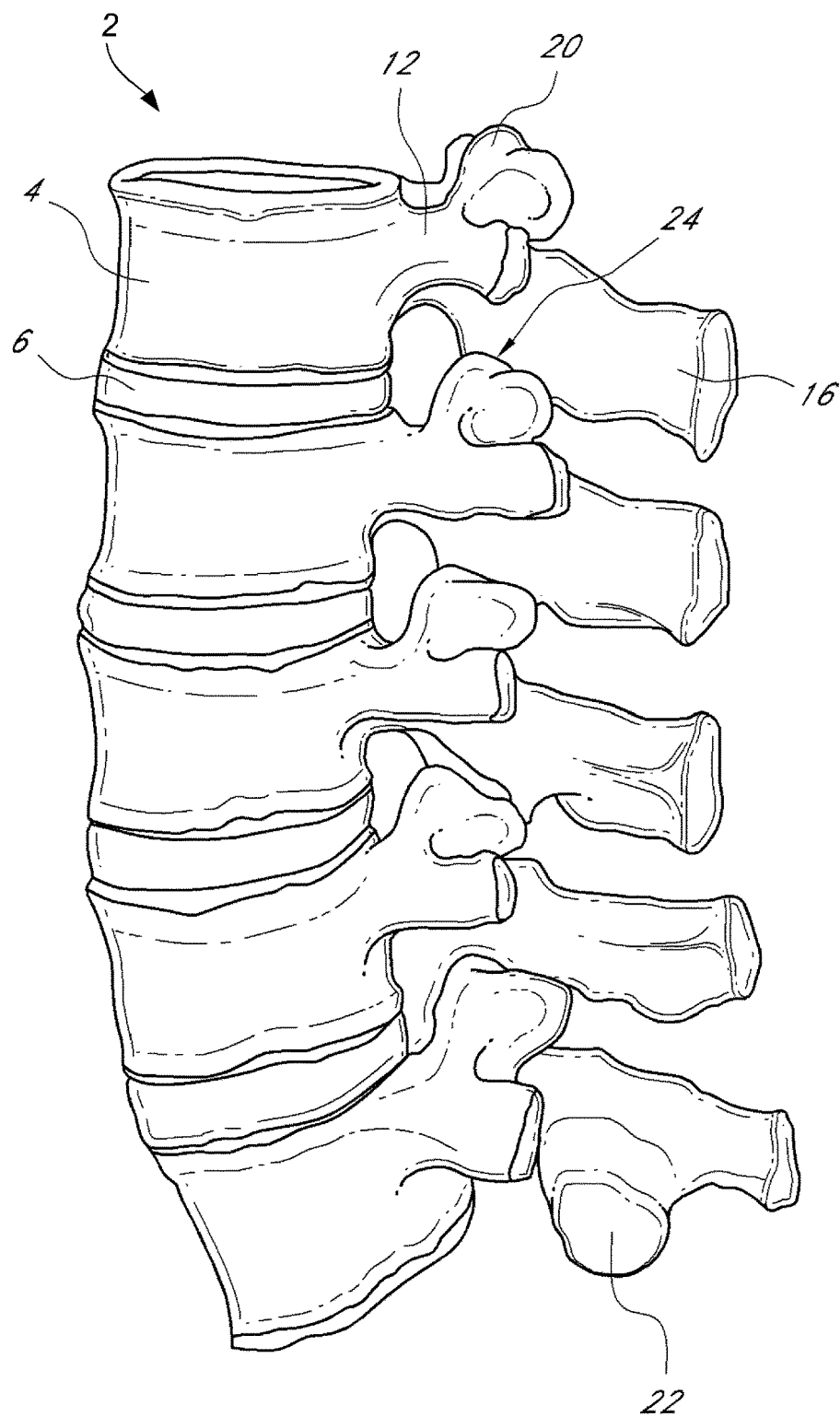
FIG. 1 is a lateral elevational view of a portion of the vertebral column.
Figure 2A:
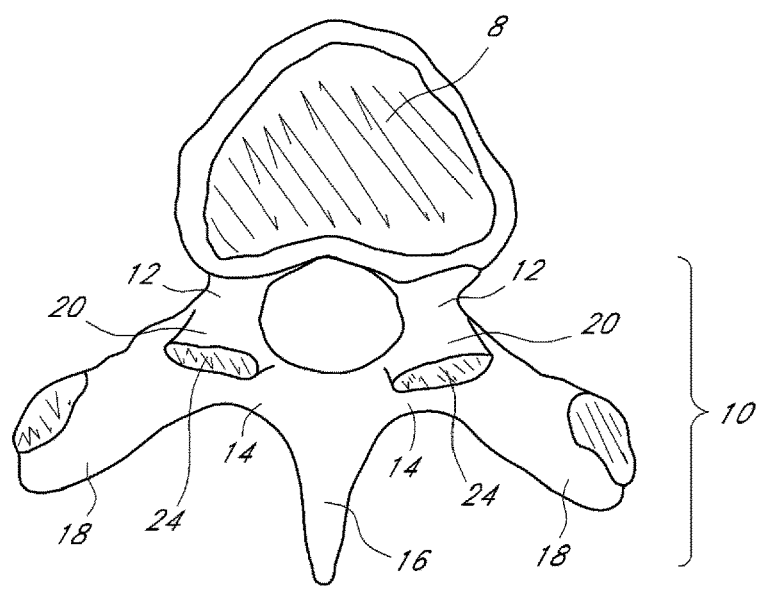
FIG. 2A is an example of a superior view of an isolated thoracic vertebra.
Figure 2B:
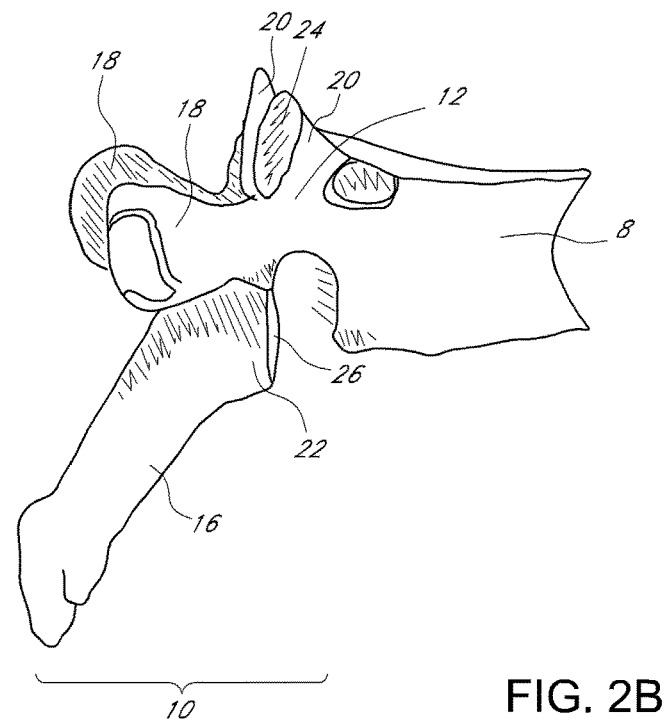
FIG. 2B is an example of a side view of an isolated thoracic vertebra.
Figure 3A:
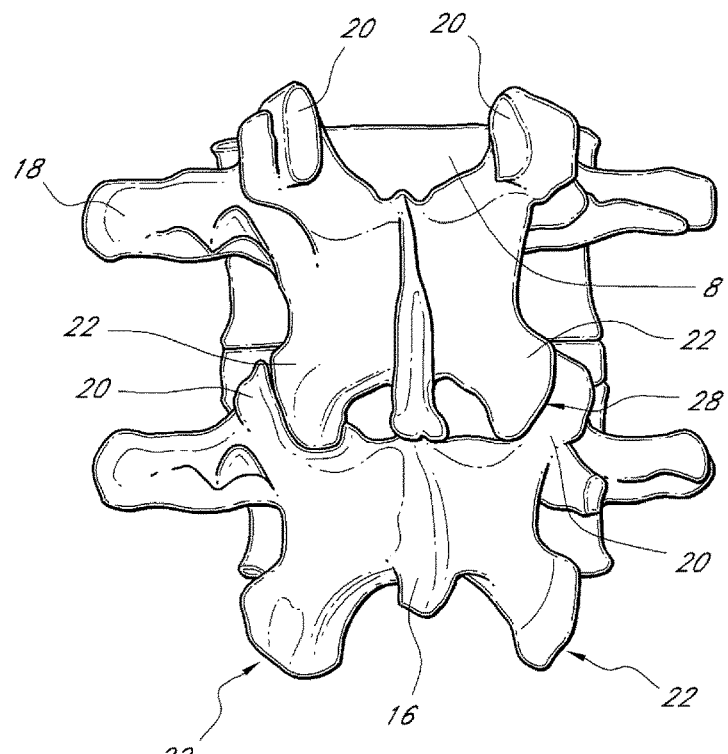
FIG. 3A is an example of a posterior elevational view of a portion of the vertebral column.
Figure 3B:
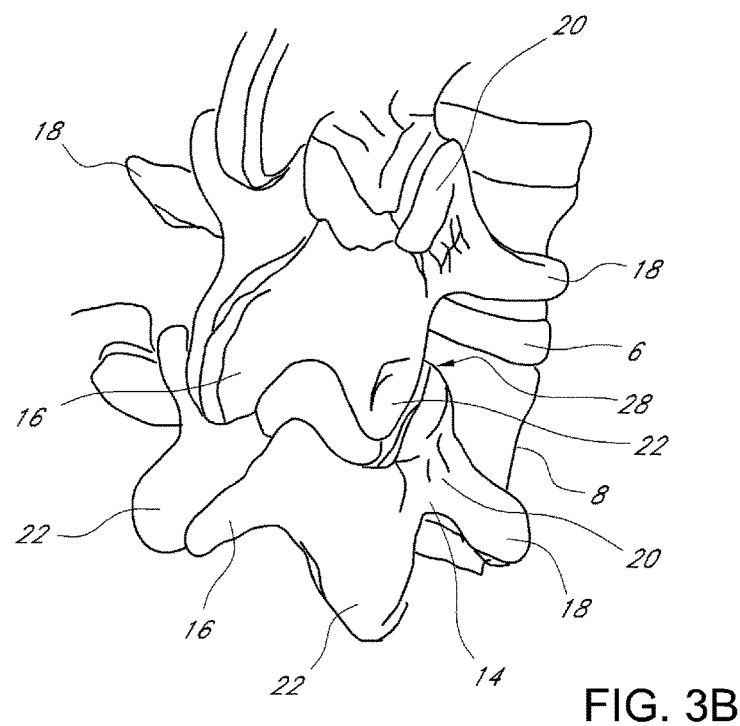
FIG. 3B is an example of a posterior-oblique elevational view of a portion of the vertebral column.
Figure 4A:
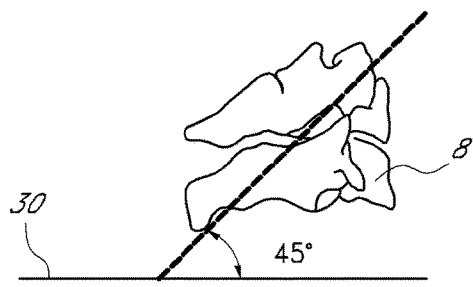
FIG. 4A is an example of a side view of a facet joint in the cervical vertebrae.
Figure 4B:
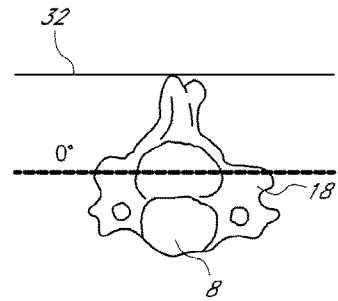
FIG. 4B is an example of a superior view of a facet joint in the cervical vertebrae.

As shown in FIG. 1, the vertebral column 2 includes a series of alternating vertebrae 4 and fibrous discs 6 that provide axial support and movement to the upper portions of the body. The vertebral column 2 typically comprises thirty-three vertebrae 4, with seven cervical (C1-C7), twelve thoracic (T1-T12), five lumbar (L1-15), five fused sacral (S1-S5) and four fused coccygeal vertebrae. FIGS. 2A and 2B depict a typical thoracic vertebra. Each vertebra includes an anterior body 8 with a posterior arch 10. The posterior arch 10 includes two pedicles 12 and two laminae 14. The two laminae 14 join posteriorly to form a spinous process 16. Projecting from each side of the posterior arch 10 is a transverse process 18, a superior process 20, and an inferior articular process 22. The facets 24, 26 of the superior processes 20 and the inferior articular processes 22 form facet joints 28 with the articular processes of the adjacent vertebrae (see FIGS. 3A and 3B). The facet joints are synovial joints with cartilaginous surfaces and a joint capsule.

Figure 5A:
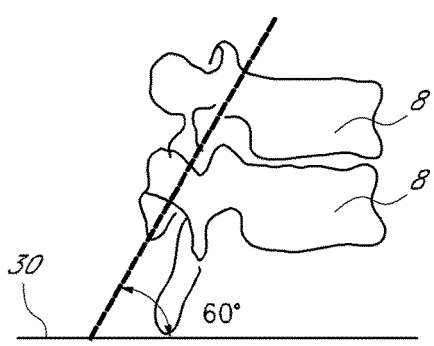
FIG. 5A is an example of a side view of a facet joint in the thoracic vertebrae.
Figure 5B:
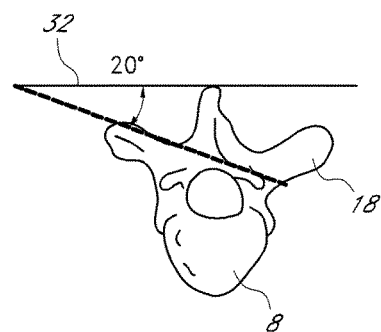
FIG. 5B is an example of a superior view of a facet joint in the thoracic vertebrae.
Figure 6A:
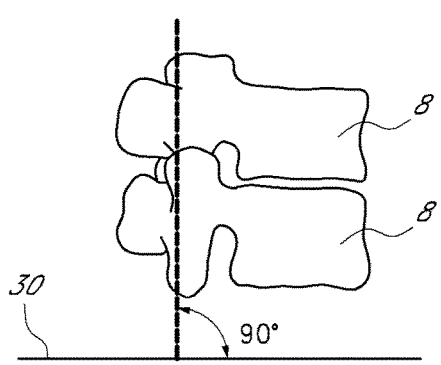
FIG. 6A is an example of a side view of a facet joint in the lumbar vertebrae.
Figure 6B:
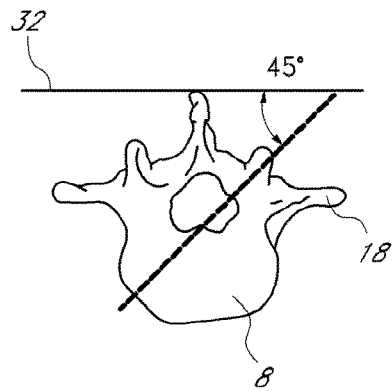
FIG. 6B is an example of a superior view of a facet joint in the lumbar vertebrae.

The orientation of the facet joints vary, depending on the level of the vertebral column. In the C1 and C2 vertebrae, for example the facet joints are parallel to the transverse plane. FIGS. 4A to 6B depict examples of the orientations of the facet joints at different levels of the vertebral column. In the C3 to C7 vertebrae examples shown in FIGS. 4A and 4B, the facets are oriented at a 45-degree angle to the transverse plane 30 and parallel to the frontal plane 32, respectively. This orientation allows the facet joints of the cervical vertebrae to flex, extend, lateral flex and rotate. At a 45-degree angle in the transverse plane 30, the facet joints of the cervical spine can guide, but do not limit, the movement of the cervical vertebrae. FIGS. 5A and 5B depict examples of the thoracic vertebrae, where the facets are oriented at a 60-degree angle to the transverse plane 30 and a 20-degree angle to the frontal plane 32, respectively. This orientation is capable of providing lateral flexion and rotation, but only limited flexion and extension. FIGS. 6A and 6B illustrate examples of the lumbar region, where the facet joints are oriented at 90-degree angles to the transverse plane 30 and a 45-degree angle to the frontal plane 32, respectively. The lumbar vertebrae are capable of flexion, extension and lateral flexion, but little, if any, rotation because of the 90-degree orientation of the facet joints in the transverse plane. The actual range of motion along the vertebral column can vary considerably with each individual vertebra.

In addition to guiding movement of the vertebrae, the facet joints also contribute to the load-bearing ability of the vertebral column. One study by King et al. Mechanism of Spinal Injury Due to Caudocephalad Acceleration, Orthop. Clin. North Am., 6:19 1975, found facet joint load-bearing as high as 30% in some positions of the vertebral column. The facet joints may also play a role in resisting shear stresses between the vertebrae. Over time, these forces acting on the facet joints can cause degeneration and arthritis.

Figure 7:
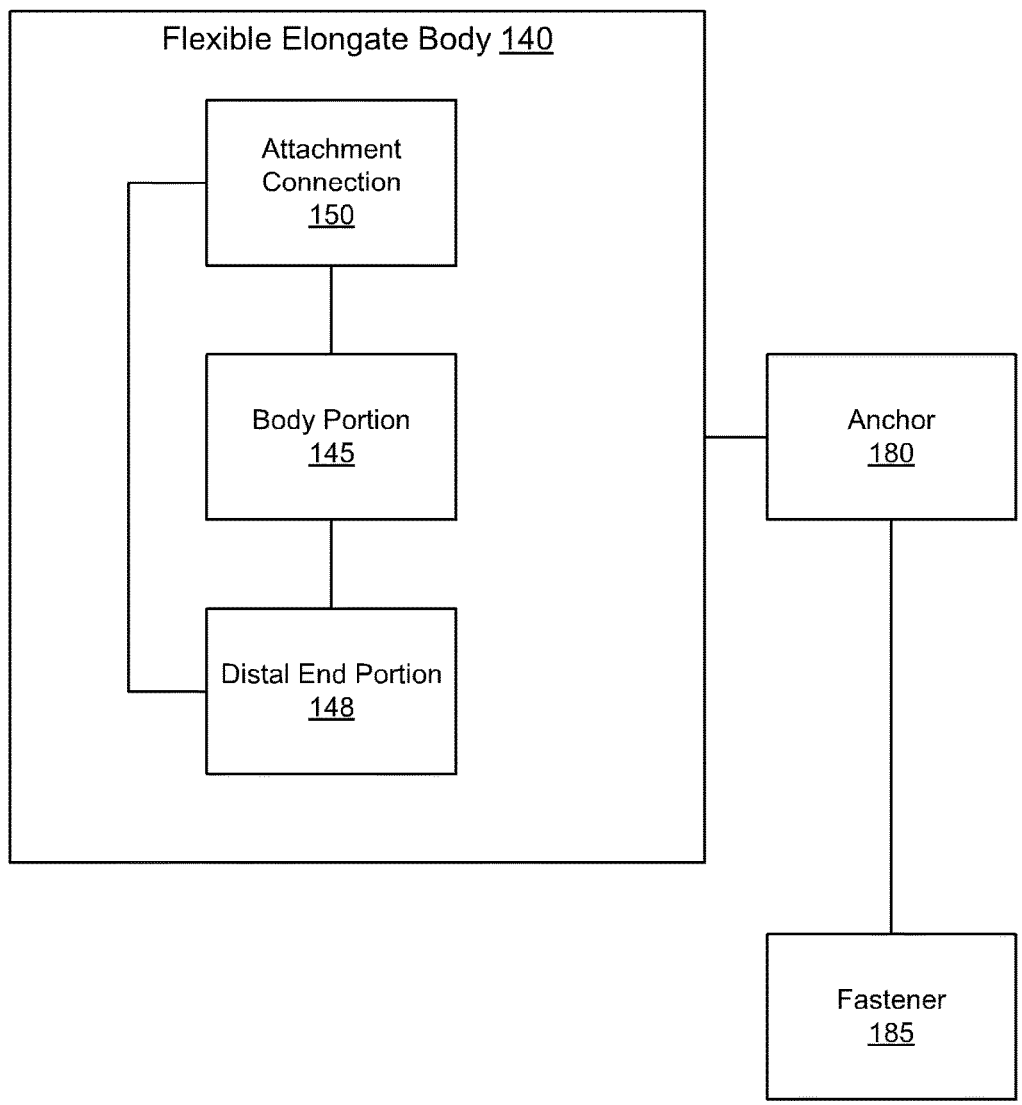
FIG. 7 is a block diagram of a flexible elongate body according to an embodiment.

In some embodiments described herein, a flexible elongate body can be anchored to a first vertebra via an anchor and can be used to stabilize and/or fixate a first vertebra to a second vertebra to reduce the pain, to reduce further degradation of a spine (e.g., a specific vertebra and/or a specific disc of a spine), and/or until the first vertebra and the second vertebra have fused. FIG. 7 is a schematic block diagram of a flexible elongate body 140 (also referred to herein as "flexible band" or simply "band") and an anchor 180, according to an embodiment. The band 140 includes at least a body portion 145, a distal end portion 148, and an attachment connection 150 (alternatively referred to herein as "fastener mechanism"). The band 140 can be formed from any suitable biocompatible material such as, for example, stainless steel, titanium, polyether ether ketone (PEEK), nylon, or the like. Moreover, the band 140 can be any suitable shape, size, or configuration. In some embodiments, the size or shape of the band 140 can be associated with an intended usage. For example, in some embodiments, a first band can be intended to stabilize and/or fixate one or more cervical vertebra and a second band can be intended to stabilize and/or fixate one or more lumbar vertebra. In this manner, the first band can have a first size that is substantially smaller than a second size of the second band. In other embodiments, the size and shape need not be associated with an intended usage.

The fastener mechanism 150 is configured to accept at least a portion of distal end portion 148 and/or the body portion 145, as further described herein. The fastener mechanism 150 is disposed at a proximal end of the band 140. In some embodiments, the fastener mechanism 150 defines a lumen (not shown in FIG. 7) configured to accept at least a portion of distal end portion 148 and/or the body portion 145. In some embodiments, the lumen of fastener mechanism 150 can have a cross-sectional area that is significantly smaller than a cross-sectional area of at least a portion of the body portion 145. In this manner, the portion of the body portion 145 can be prevented from advancing through fastener mechanism 150. In some embodiments, the fastener mechanism 150 can include a ratchet (not shown in FIG. 7) configured to engage a surface of the distal end portion 148 and/or the body portion 145. In this manner, the fastener mechanism 150 can be configured to allow the distal end portion 148 and/or the body portion 145 to advance through fastener mechanism 150 in a first direction and substantially limit the movement of the distal end portion 148 and/or the body portion 145 in a second direction, opposite the first direction.

The body portion 145 is a linear elongate that extends from a portion of the fastener mechanism 150. More specifically, the body portion 145 of the band 140 can be monolithically formed with the fastener mechanism 150 such that the body portion 145 is a linear elongate portion between the fastener mechanism 150 and the distal end portion 148. In other embodiments, the body portion 145 can be coupled to the fastener mechanism 150 in any suitable manner (e.g., coupled via an adhesive, a weld, a friction fit, a threaded fit, or the like). The body portion 145 can be any suitable configuration. For example, in some embodiments, the body portion 145 can have a cross-sectional shape that is polygonal (e.g., square, rectangular, trapezoidal, etc.) or oval (e.g., circular, elliptical, oblong, etc.). In some embodiments, the cross-sectional shape of the body portion 145 can be associated with one or more characteristics of the bone or bone portion against which the body portion 145 may contact. For example, while the body portion 145 can have a substantially square cross-sectional shape, a set of edges of the body portion 145 can be rounded, partially rounded, and/or otherwise shaped to compliment the shape of a bone or bone portion, and/or to reduce digging or grinding into the bone or bone portion. In this manner, use of band 140 may cause little or no damage to the bone or bone portions contacted by band 140.

In some embodiments, the body portion 145 can define a substantially uniform cross-sectional area along a longitudinal axis (e.g., a centerline) of the band 140. In other embodiments, the cross-sectional area of the body portion 145 can vary along the longitudinal axis (centerline) of the band 140. For example, in some embodiments, the body portion 145 can have a cross-sectional area that is substantially tapered (i.e., reduced) from a proximal end (e.g., adjacent the fastener mechanism 150) to a distal end (e.g., adjacent the distal end portion 148). In some embodiments, the cross-sectional area of the body portion 145 can be associated with the cross-sectional area of the lumen defined by the fastener mechanism 150 (the attachment connection 150 described above). In this manner, at least a portion of the body portion 145 can have a cross-sectional area that is sufficiently small such that the body portion 145 can be at least partially disposed within the lumen of the fastener mechanism 150.

The body portion 145 can be configured to include a gear rack (not shown in FIG. 7) configured to engage the ratchet (not shown in FIG. 7) of the fastener mechanism 150. As described above, the gear rack can be configured to engage the ratchet of the fastening member 150 such that the ratchet allows the body portion 145 to travel through the fastener mechanism 150 in the first direction and substantially limits the movement of the body portion in the second direction, opposite the first direction. In some embodiments, the gear rack can be configured to include a set of individual gears that extend from a surface of the body portion 145. In other embodiments, the body portion 145 can define the set of individual gears (e.g., the gears each include a top surface that is disposed at or below a surface of the body portion 145). The gears included in the set of gears can be any suitable shape, size, or configuration. For example, in some embodiments, the gears are substantially cubed. In other embodiments, the gears can be triangular such that the gears form, for example, teeth. In this manner, the gears included in the gear rack can be configured to engage the ratchet of the fastener mechanism 150, as described above.

The distal end portion 148 is configured to extend from the body portion 145 of the band 140. More specifically, the distal end portion 148 is disposed adjacent the distal end of the body portion 145 such that the body portion 145 is disposed between the distal end portion 148 and the fastener portion 150. In some embodiments, the distal end portion 148 can have a cross-sectional area that is substantially similar to the cross-sectional area of the body portion 145. In other embodiments, the distal end portion 148 can have a cross-sectional area that is substantially smaller than the cross-sectional area of the body portion 145. In such embodiments, the distal end portion 148 and the body portion 145 can collectively define a discontinuity defining a stepwise reduction in the cross-sectional area. In other embodiments, the body portion 145 and/or the distal end portion 148 can define a tapered portion such that the band 140 is tapered between smaller cross-sectional area of the distal end portion 148 and the larger cross-sectional area of the body portion 145.

While not shown in FIG. 7, in some embodiments, the distal end portion 148 can include a gear rack that is substantially similar to the gear rack of the body portion 145. In this manner, the gear rack can extend substantially continuously across a portion of the distal end portion 148 and a portion of the body portion 145. In other embodiments, the distal end portion 148 of the band 140 need not include or define a gear rack.

The anchor 180 is configured to receive a fastener 185 to secure the band 140 to a bone portion. In some embodiments, the anchor 180 is monolithically formed with the band 140. For example, in some embodiments, the anchor 180 can be disposed on or within the body portion 145 and can define an aperture (not shown in FIG. 7) configured to receive the fastener 185 (e.g., a mechanical fastener such as a screw, bolt, staple, nail, etc.). In other embodiments, the anchor 180 is a protrusion extending from the body portion 145 in a substantially perpendicular direction (e.g., relative to the longitudinal axis of the band 140). In other embodiments, the anchor 180 can be a protrusion that extends in an angular direction from the body portion 145 or the distal end portion 148 (e.g., non-perpendicular to the body portion 145 or the distal end portion 148). In some embodiments, the anchor 180 can be a portion of the band 140 including a surface configured to receive the fastener 185. For example, in such embodiments, the anchor 180 can have a surface configured to receive a biocompatible adhesive or tape.

In some embodiments, the anchor 180 can be formed independently from the band 140 and can be at least partially disposed about the band 140 to secure the band 140 to the bone portion. For example, in some embodiments, the anchor 180 can define a second aperture configured to receive the distal end portion 148 of the band 140. In this manner, the anchor 180 can define a strap or loop configured to be slid into any suitable position along the distal end portion 148 and/or the body portion 145. In some embodiments, the anchor 180 can form a hook (e.g., a J-hook, an L-hook, etc.). In this manner, the anchor 180 can be configured to engage at least three sides of the band 140. In such embodiments, the anchor 180 can include an edge configured to engage a surface of the bone portion to retain the band 140 between the edge and the fastener 185 when the fastener 185 is disposed within the second aperture (e.g., defined by the anchor 180) and the bone portion, as described in further detail herein.

In use, the band 140 can be configured, for example, to stabilize a vertebra (e.g., a first vertebra) and/or a second vertebra by securing an articular process of the first vertebra to an articular process of a second vertebra. More specifically, the band 140 can be configured to stabilize the first vertebra and/or a second vertebra by securing an articular process of the first vertebra to an articular process of a second vertebra by securing a facet of the articular process of the first vertebra with a facet of the articular process of the second vertebra. For example, the band 140 can be placed into a suitable position relative to the first vertebra and/or the second vertebra, and the distal end portion 148 of the band can be inserted into the lumen of the fastener member 150 such that the body portion 145 substantially encircles at least a portion of the first vertebra and the second vertebra. Similarly stated, the distal end portion 148 can be inserted in to the lumen of the fastener mechanism 150 such that the band 140 forms a loop about the articular process of the first vertebra and the articular process of the second vertebra. In this manner, the distal end portion 148 and/or the body portion 145 can be advanced through the lumen of the fastener mechanism 150 such that the volume disposed within the loop formed by the band 140 is reduced. Thus, the band 140 exerts a compressive force on the articular process of the first vertebra and the articular process of the second process. While not shown in FIG. 7, in some embodiments, a spacer can be disposed between the articular process of the first vertebra and the articular process of the second process such that a desired distance between the articular process of the first vertebra and the articular process of the second process is maintained. In some embodiments, the spacer can include and/or define a portion configured to reduce slippage of the band 140 along a surface of the first vertebra and/or the second vertebra. Examples of spacers are further defined below with respect to specific embodiments.

With the band 140 at least partially tightened about the articular process of the first vertebra and the articular process of the second vertebra, the fastener 185 can be inserted into the anchor 180 and advanced into a portion of the articular process of the first vertebra and/or second vertebra. In some embodiments, the fastener 185 can be advanced through a pre-drilled hole of the articular process. In other embodiments, the fastener 185 can be configured to self-tap into the articular process (e.g., when the fastener is a self taping screw). In this manner, the anchor 180 can be affixed to the articular process of the first vertebra and/or the second vertebra such that the anchor 180 secures the band 140 to the first vertebra and/or the second vertebra. In this manner, the distal end portion 148 and/or the body portion 145 can be advanced through the lumen defined by the fastener mechanism 150 to stabilize and/or fixate the first vertebra to the second vertebra. Furthermore, by affixing the anchor 180 to the first vertebra and/or the second vertebra, the anchor 180 can substantially reduce slippage of the band 140 relative to the first vertebra and/or the second vertebra.

While not explicitly described above, in embodiments wherein the anchor 180 is independently formed, the anchor 180 can be disposed about the distal end portion 148 and/or the body portion 145 prior to inserting the distal end portion 148 into the lumen of the fastener member 150. While being described above as being partially tightened about the first vertebra and the second vertebra prior to affixing the anchor 180, in other embodiments, the anchor can be affixed to the first vertebra and/or the second vertebra prior to inserting the distal end portion 148 into the fastener mechanism 150. Conversely, in some embodiments, the band 140 can be tightened to a desired amount prior to the anchor 180 being affixed to the first vertebra and/or the second vertebra.

FIG. 8A is a side view and FIG. 8B is a top view of a flexible elongate body 240 (also referred to herein as "band") according to an embodiment. The band 240 can be similar to the band 140 described above and can include similar components. For example, the band 240 includes an attachment connection 250 (also referred to herein as "fastener mechanism") including a ratchet 262, a body portion 245 including a gear rack 247, and a distal end portion 248. Accordingly, components of the band 240 that are similar to corresponding components of the band 140 described above with reference to FIG. 7 are not described in further detail herein.

As shown in FIG. 8A, each gear 264 included in the gear rack 247 includes a cross sectional area that is rectangular in shape. Said another way, each gear 264 can be a rectangular protrusion configured to extend from a surface of the band 240 (e.g., the body portion and/or the distal end portion 248). The gear rack 247 is configured to engage the ratchet 262 of the fastener mechanism 250, as further described herein. The fastener mechanism 250 defines a lumen 266. The lumen 266 can be any suitable shape, size, or configuration. For example, as shown in FIG. 8B the lumen 266 can have a substantially circular cross-sectional area. The ratchet 262 extends from an inner surface of the fastener member 250 such that the ratchet 262 substantially reduces the size (e.g., the perimeter, circumference, and/or cross-sectional area) of the lumen 266. In this manner, the ratchet 266 can engage the gear rack 247. More specifically, as described in detail with reference to FIG. 7, the distal end portion 248 can be inserted into the lumen 266 of the fastener mechanism 250 and advanced in a first direction such that the gear rack 247 of the distal end portion 248 engages the ratchet 262. In some embodiments, the distal end portion 248 can be advanced through the lumen 266 a sufficient distance such that a portion of the body portion 245 is disposed within the lumen 266. In such embodiments, a portion of the gear rack 247 disposed on (e.g., included in or defined by) the body portion 245 can engage the ratchet 262. In this manner, the arrangement of the ratchet 262 and the gear rack 247 can be such that the distal end portion 248 can be moved in the first direction, thereby tightening the band 240, and the distal end portion 248 can be prevented from moving in a second direction, opposite the first direction, thereby preventing the band 240 from loosening.

The band 240 can be used in any suitable procedure to stabilize and/or fixate a first bone portion to a second bone portion. For example, in some embodiments, the band 240 can be disposed about an articular process of a first vertebra and an articular process of a second vertebra. In this manner, the distal end portion 248 and/or the body portion 245 can be positioned within the lumen 266 of the fastener mechanism 250 such that the band 240 forms a loop of suitable tightness about the first vertebra and the second vertebra. The band 240 can be used in conjunction with any suitable anchor configured to facilitate the stabilization and/or fixation of the first vertebra to the second vertebra and further configured to reduce potential slippage of the band 240 relative to the first vertebra and/or the second vertebra (as described in detail above with reference to FIG. 7).

In some embodiments, the band 240 can be used in any procedure described in or similar to those in U.S. patent application Ser. No. 12/859,009; filed Aug. 18, 2010, and titled "Vertebral Facet Joint Drill and Method of Use" (referred to as "the '009 application"), the disclosure of which is incorporated herein by reference in its entirety. In some embodiments, the band 240 can be used in conjunction with a spacer such as those described in the '009 application. For example, the spacer can be implanted and deployed to restore the space between facets of a superior articular process of a first vertebra and an inferior articular process of an adjacent vertebra. The spacer can be implanted and deployed to help stabilize adjacent vertebrae with adhesives and/or to deliver a medication. For example, in some embodiments, the spacer can be at least temporarily maintained in a desired position via an adhesive while the band 240 is positioned relative to the first vertebra and/or second vertebra. In some embodiments, an adhesive can be used in conjunction with the band 240 to stabilize and/or fixate the first vertebra to the second vertebra.

In some embodiments, the spacer can be, for example, substantially disc shaped. In other embodiments, the spacer can be other shapes, e.g., square, elliptical, or any other shape. The spacer can include a first side and a second side. The first side and/or the second side can be, for example, convex, concave, or flat. Said another way, the first side of the spacer can be concave, convex, or flat, and the second side of the spacer can be concave, convex, or flat, for example, the first side can be concave and the second side concave, the first side can be concave and the second side convex, etc. The spacer can include the same materials as band 140. In some embodiments, the spacer can include substances configured to release medication and/or increase the stability of a vertebra and/or band 140. As discussed above, the substances can include a medicine(s) and/or an adhesive(s).

Figure 9A:
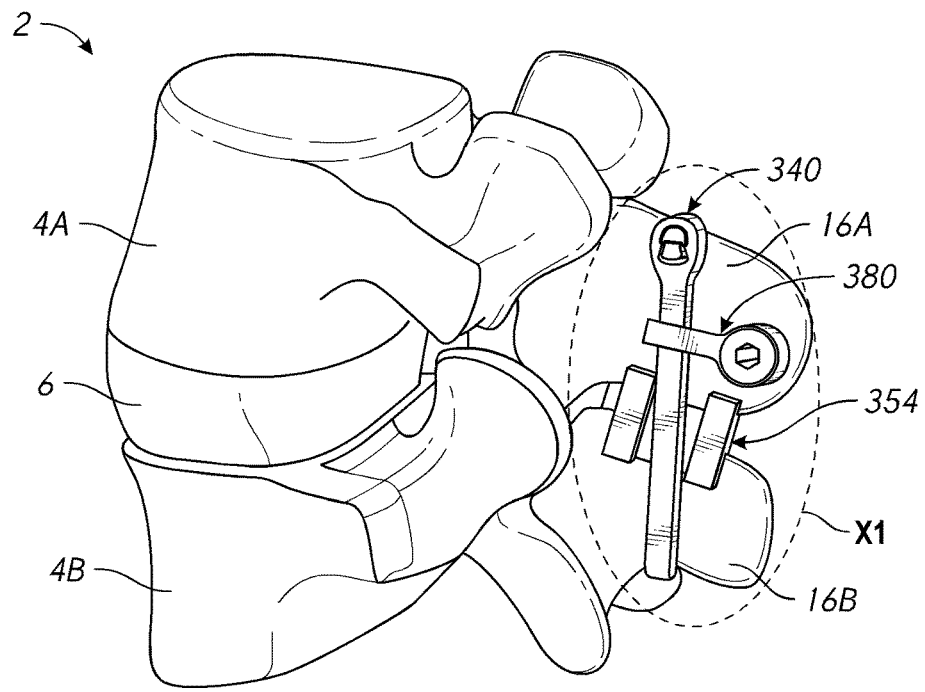
FIG. 9A is a posterior perspective view of a portion of the vertebral column depicting a stabilized vertebra including a flexible elongate body, a spacer, and an anchor, according to an embodiment.
Figure 9B:
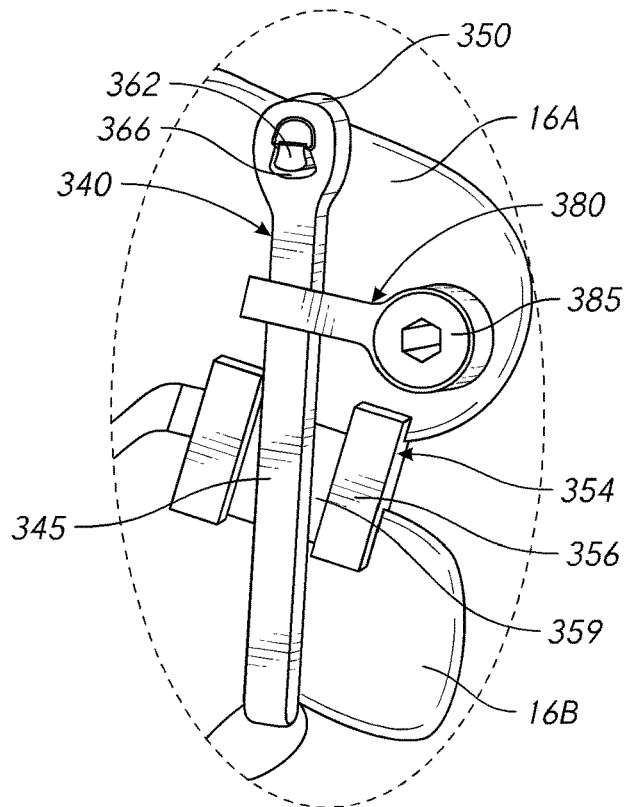
FIG. 9B is an enlarged view of a portion of the vertebral column of FIG. 9A identified as region $X_1$.
Figure 10A:
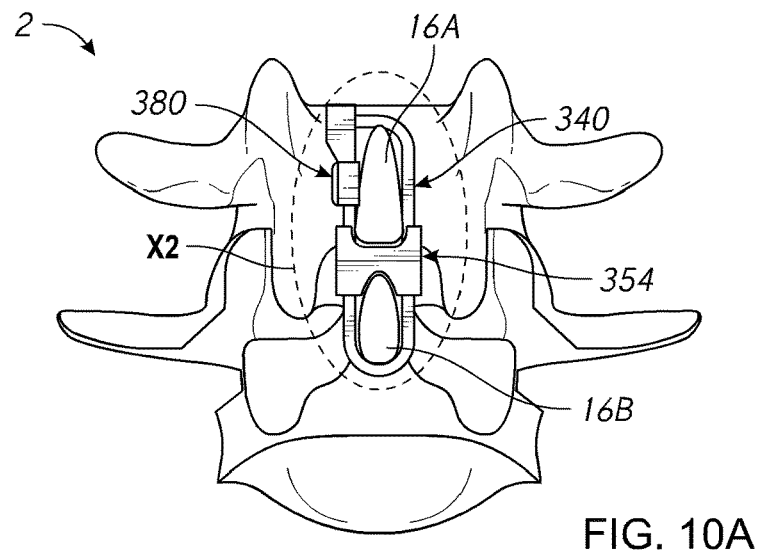
FIG. 10A is a posterior view of the portion of the vertebral column of FIG. 9A depicting the stabilized vertebra including the flexible elongate body, the spacer, and the anchor.
Figure 10B:
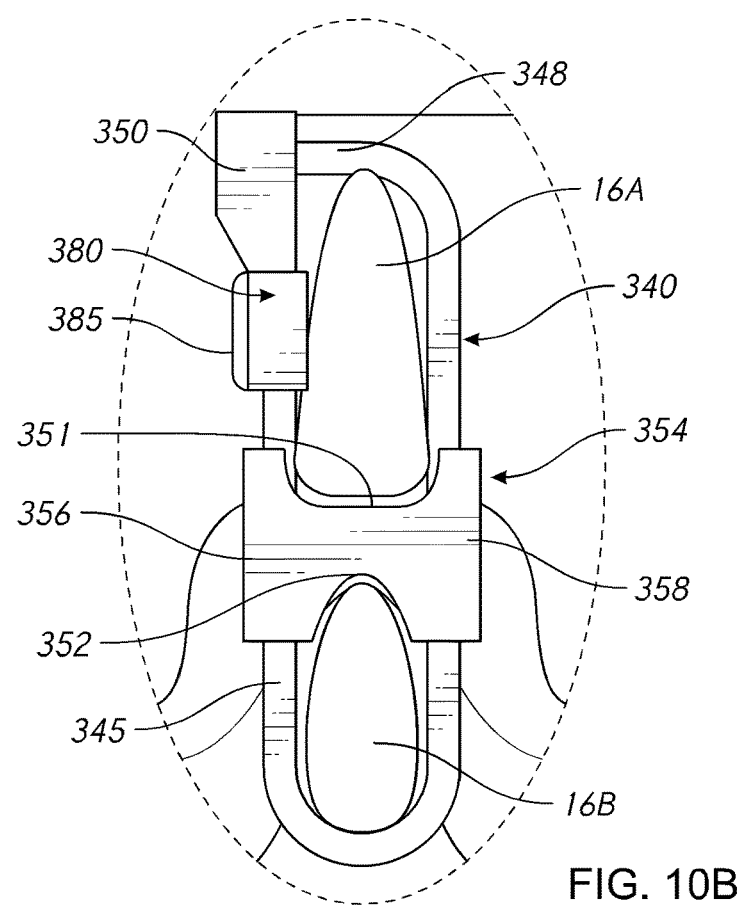
FIG. 10B is an enlarged view of a portion of the vertebral column of FIG. 10A identified as region $X_2$.

FIGS. 9A-10B illustrate a flexible elongate body 340 (also referred to herein as "band"), an anchor 380, and a spacer 354 collectively used to stabilize adjacent vertebrae according to an embodiment. As shown in FIG. 9A, the band 340 can be used to stabilize a first vertebra 4A and a second vertebra 4B via the spinous articular process 16A (also referred to herein as "process 16A") of the first vertebra 4A and the spinous articular process 16B (also referred to herein as "process 16B") of the second vertebra 4B. The band 340 can be similar to band 140 described above with reference to FIG. 7 and can include similar components. By way of example, band 340 includes a fastener mechanism 350 (FIG. 9B), a body portion 345 (FIG. 9B), and a distal end portion 348 (FIG. 10B). As shown in FIGS. 9A-10B, the band 340 can be monolithically constructed in an elongate shape and can have a substantially rectangular cross-sectional shape. More specifically, the band 340 can have a substantially rectangular shape including rounded edges configured to reduce digging or grinding into the bone or portion thereof.

The fastener mechanism 350 defines a lumen 366 and includes a ratchet 362. The lumen 366 of the fastener mechanism 350 receives the distal end portion 348 of the band 340 such that the body portion 345 forms a loop that substantially encircles the process 16A of the first vertebra 4A and the process 16B of the second vertebra 4B. While not shown in FIGS. 9A-10B, the band 340 includes a gear rack that can be similar to or the same as the gear racks described above in the previous embodiments. In this manner, the ratchet 362 is configured to engage the gear rack of the band 340 to maintain the distal end portion 348 of the band 340 within the lumen 366 (as described in detail above).

The anchor 380 is configured to substantially surround a portion of the band 340 as shown in FIGS. 9A and 9B. More specifically, the anchor 380 can be a hook (e.g., a J-hook or the like) configured to substantially surround the band 340 on at least three sides (e.g., all of the sides of the band 340 except the side disposed adjacent the first vertebra 4A). The anchor 380 defines an aperture (not shown in FIGS. 9A-10B) configured to receive a fastener 385. In this manner, the fastener 385 can be advanced into the process 16A of the first vertebra 4A to affix the anchor 380 thereto. Moreover, with the anchor 380 disposed about the portion of the band 340, the anchor 380 can limit the movement of the band 340 relative to the first vertebra 4A and the second vertebra 4B (e.g., in the posterior or anterior direction).

The spacer 354 is disposed between the process 16A of the first vertebra 4A and the process 16B of the second vertebra 4B. The spacer 354 can be any suitable shape, size, or configuration. For example, as shown in FIGS. 10A and 10B, the spacer 354 can be substantially rectangular and can include a first indentation 351, configured to receive a portion of the process 16A, and a second indentation 352, configured to receive a portion of the process 16B. Thus, the first indentation 351 is disposed opposite the second indentation 352 and a desired distance is defined therebetween. For example, in some embodiments, the distance between the first indentation 351 and the second indentation 352 is associated with a desired distance between the process 16A of the first vertebra and the process 16B of the second vertebra 4B. Expanding further, when the band 340 is tightened (e.g., the distal end portion 348 is advanced through the fastener mechanism 350), the spacer 354 can be configured to limit the tightening of the band 340 such that the desired distance between the process 16A and the process 16B is retained. In this manner, the spacer 354 can substantially limit undue pressure on the disc 6 (FIGS. 9A and 10A), an artificial disk, or a cage disposed between the first vertebra 4A and the second vertebra 4B, otherwise induced by over tightening the band 340.

As shown in FIG. 10B, the spacer 354 further includes a first side wall 356 and a second side wall 358. The first side wall 356 and the second side wall 358 can be configured to each define a channel 359 (shown on the first side wall 356 in FIGS. 9A and 9B). The channel 359 can receive a portion of the band 340 such that the walls defining the channel 359 substantially limit a posterior and/or an anterior movement of the portion of the band 340 (e.g., the walls form a barrier that limit the movement of the band 340 relative to the spacer 354). In this manner, the spacer 354 can reduce slippage of the band 340 relative to the process 16A and/or process 16B that may otherwise occur during tightening of the band 340. While the anchor 380 is shown as being disposed at a posterior position relative to the band 340, in other embodiments, the anchor 380 can be disposed in an anterior configuration wherein the fastener 385 is disposed on an anterior portion of the process 16A relative to the band 340.

Figure 11A:
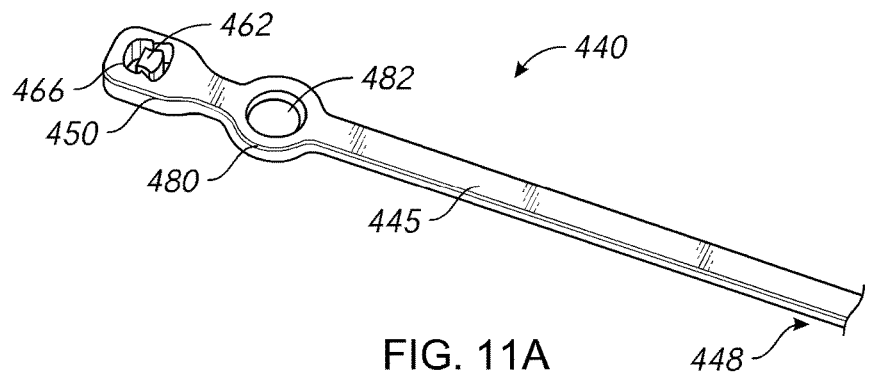
FIGS. 11A-11C are various views of a flexible elongate body according to another embodiment.
Figure 11B:
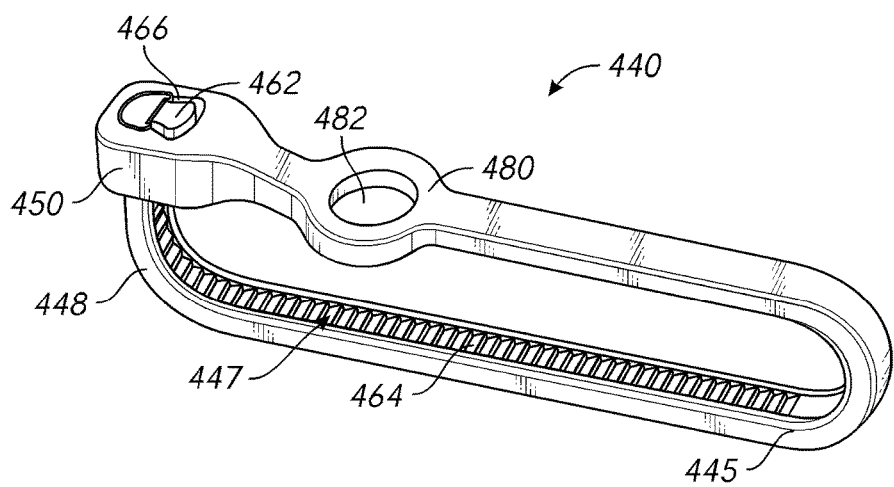
Figure 11C:
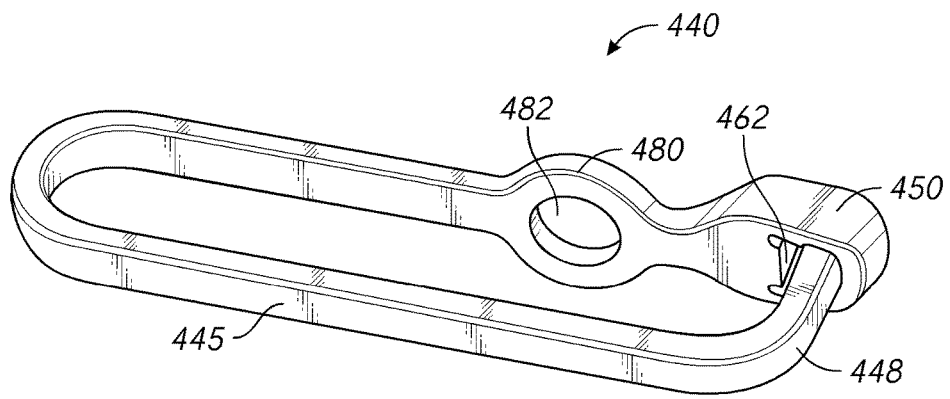

While the anchor 380 is shown as being independently formed from the band 340, in other embodiments, an anchor can be monolithically formed with a band. For example, FIGS. 11A-11C illustrate a flexible elongate body 440 (also referred to herein as "band") according to an embodiment. The band 440 can be similar to band 140 described above with reference to FIG. 7 and can include similar components. By way of example, band 440 includes a fastener mechanism 450, a body portion 445, a distal end portion 448, and an anchor portion 480. As shown in FIGS. 11A-11C, the band 440 can be monolithically constructed in an elongate shape and can have a substantially rectangular cross-sectional shape. More specifically, the band 440 can have a substantially rectangular shape including rounded edges configured to reduce digging or grinding into the bone or portion thereof. The fastener mechanism 450 defines a lumen 466 and includes ratchet 462. The body portion 445 includes a gear rack 447 having a set of gears 464. In this manner, the distal end portion 448 can be inserted into the lumen 466 of the fastener member 450 such that the gear rack 447 engages the ratchet 462, as described in detail above. The anchor portion 480 is monolithically formed with the band 440. More specifically, the anchor portion 480 can be a substantially annular portion of the band 480 configured to define an aperture 482. The aperture 482 can receive a fastener 485 (FIGS. 12A and 12B), as further described herein.

Figure 12A:
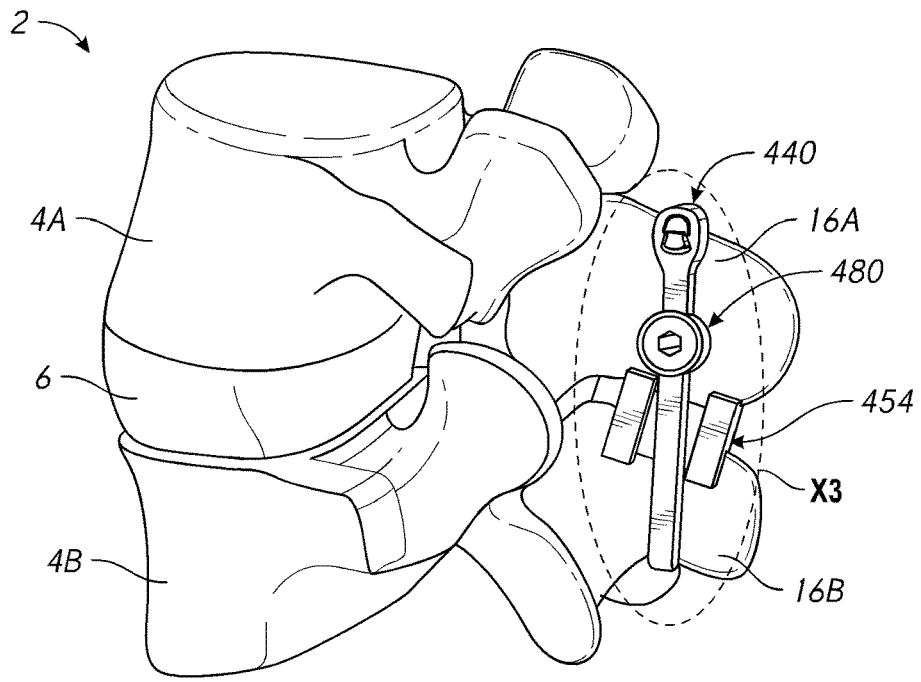
FIG. 12A is a posterior perspective view of a portion of the vertebral column depicting a stabilized vertebra including the flexible elongate body illustrated in FIGS. 11A-11C and a spacer.
Figure 12B:
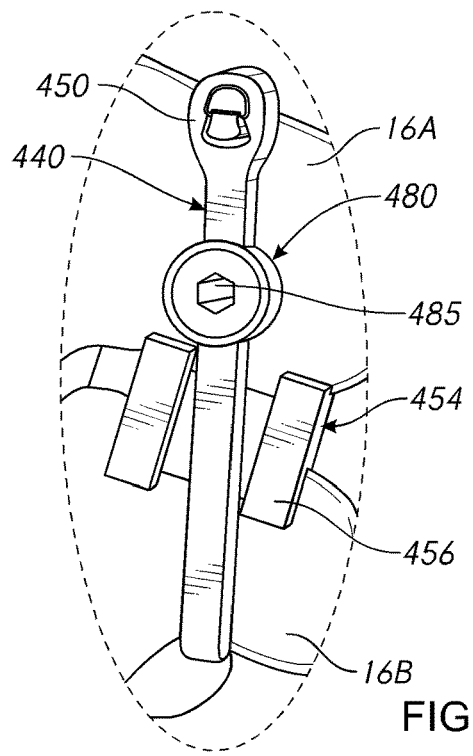
FIG. 12B is an enlarged view of a portion of the vertebral column of FIG. 12A identified as region $X_3$.

As shown in FIGS. 12A and 12B, the band 440 can be used to stabilize a first vertebra 4A and a second vertebra 4B via the spinous articular process 16A (also referred to herein as "process 16A") of the first vertebra 4A and the spinous articular process 16B (also referred to herein as "process 16B") of the second vertebra 4B. More specifically, the lumen 466 of the fastener mechanism 450 can receive the distal end portion 448 of the band 440 such that the body portion 445 forms a loop that substantially encircles the process 16A of the first vertebra 4A and the process 16B of the second vertebra 4B (as described in detail above). The fastener 485 can be inserted into the aperture 482 (FIGS. 11A-11C) and advanced into the process 16A of the first vertebra 4A to affix the anchor portion 480 thereto. In some embodiments, the fastener 485 can be inserted into the aperture 482 and at least partially advanced into the process 16A of the first vertebra 4A prior to the distal end portion 448 of the band 440 being inserted into the lumen 466 of the fastener mechanism 450. In some embodiments, the fastener 485 can be advanced into the process 16A concurrently with the distal end portion 448 being advanced through the lumen 466.

With the anchor portion 480 affixed to the process 16A via the fastener 485, movement of the band 440 in the anterior and/or posterior direction, relative to the process 16A is substantially limited. In addition, a spacer 454 can be disposed between the process 16A of the first vertebra 4A and the process 16B of the second vertebra 4B prior to tightening the band 440 about the process 16A of the first vertebra 4A and the process 16B of the second vertebra 4B. For example, in some embodiments, the spacer 454 can be disposed between the process 16A of the first vertebra 4A and the process 16B of the second vertebra 4B after advancing the fastener 485 into the process 16A and prior to advancing the distal end portion 448 of the band 440 through the lumen 466. In other embodiments, the spacer 454 can be disposed between the process 16A of the first vertebra 4A and the process 16B of the second vertebra 4B prior to the insertion of the fastener 454 in the process 16A and prior to the insertion of the distal end portion 448 into the lumen 466. In still other embodiments, the spacer 454 can be disposed between the process 16A of the first vertebra 4A and the process 16B of the second vertebra 4B after the fastener 485 is advanced into the process 16A and after the band 440 is partially tightened. The spacer 454 can be similar to the spacer 354 described above with reference to FIGS. 9A-10B. Therefore, the form of spacer 454 is not described in detail herein. As described above, the spacer 454 can reduce slippage of the band 440 relative to the process 16A and/or process 16B that may occur during tightening of the band 440.

Figure 13A:
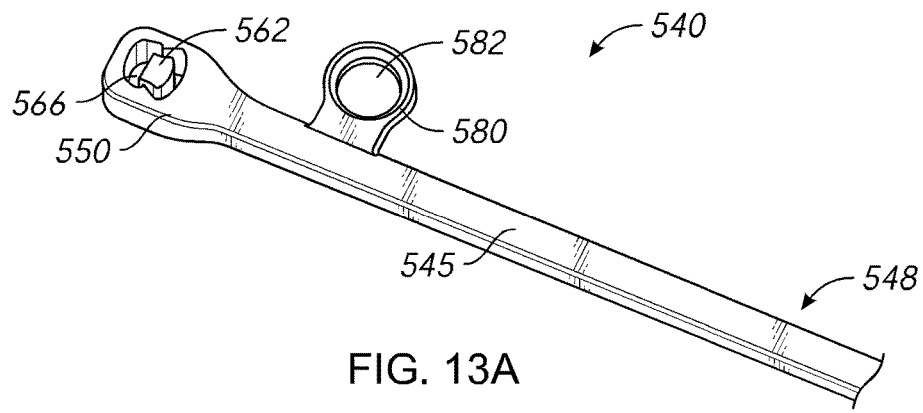
FIGS. 13A-13C are various views of a flexible elongate body according to yet another embodiment.
Figure 13B:
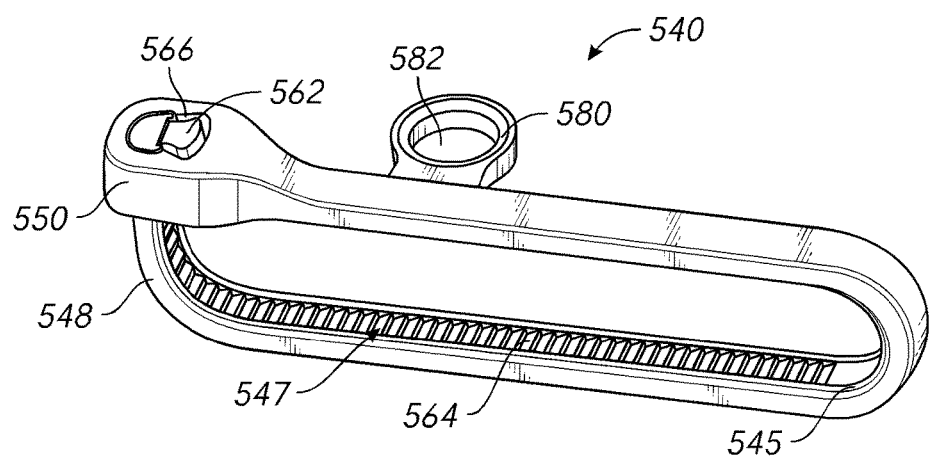
Figure 13C:
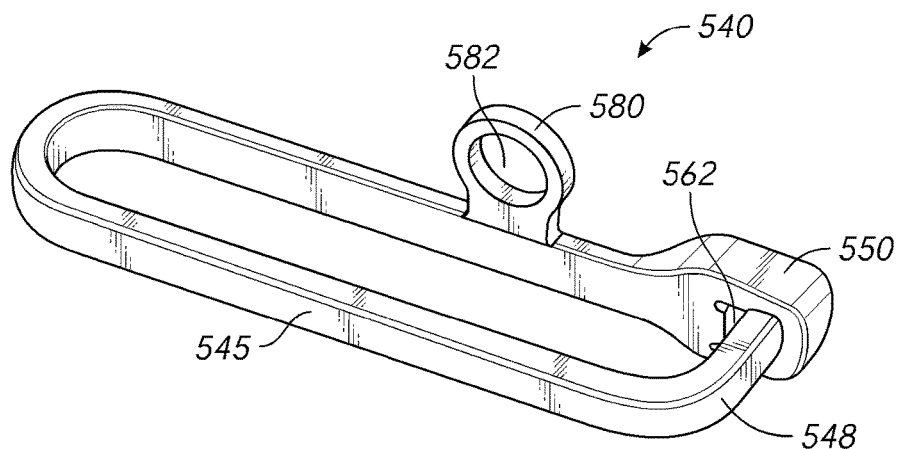

While the anchor portion 480 is shown in FIGS. 11A-12B as being substantially aligned with the body portion 445 of the band 440 (e.g., a center point of the annular shaped anchor portion 480 is positioned on a longitudinal axis or centerline of the band 440), in some embodiments, a flexible elongate body can include an anchor portion that is not positioned on a longitudinal axis or centerline. For example, FIGS. 13A-13C illustrate a flexible elongate body 540 (also referred to herein as "band") according to an embodiment. The band 540 can be similar to band 140 described above with reference to FIG. 7 and can include similar components. By way of example, band 540 includes a fastener mechanism 550, a body portion 545, a distal end portion 548, and an anchor portion 580. As shown in FIGS. 13A-13C, the band 540 can be monolithically constructed in an elongate shape and can have a substantially rectangular cross-sectional shape. More specifically, the band 540 can have a substantially rectangular shape including rounded edges configured to reduce digging or grinding into the bone or portion thereof. The fastener mechanism 550 defines a lumen 566 and includes ratchet 562. The body portion 545 includes a gear rack 547 having a set of gears 564. In this manner, the distal end portion 548 can be inserted into the lumen 566 of the fastener member 550 such that the gear rack 547 engages the ratchet 562, as described in detail above.

The anchor portion 580 is monolithically formed with the band 540. More specifically, the anchor portion 580 can be a lateral protrusion extending from a side of the band 540. For example, in some embodiments, the anchor portion 580 can extend substantially perpendicularly from a side of the band 540. In other embodiments, the anchor portion 580 can extend from the side of the band 540 at any suitable angular orientation (i.e., an angular orientation other than the perpendicular orientation (e.g., other than 90 degrees)). The anchor portion 580 can be substantially annular such that the anchor portion 580 defines an aperture 582. The aperture 582 can receive a fastener 585 (FIGS. 14A and 14B), as further described herein.

Figure 14A:
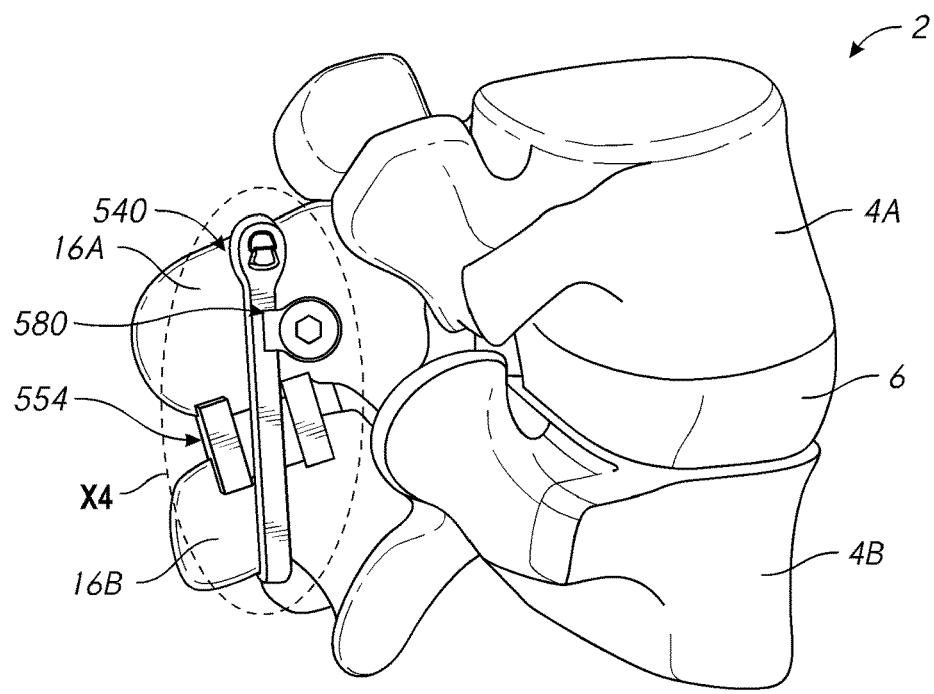
FIG. 14A is a posterior perspective view of a portion of the vertebral column depicting a stabilized vertebra including the flexible elongate body illustrated in FIGS. 12A-12C.
Figure 14B:
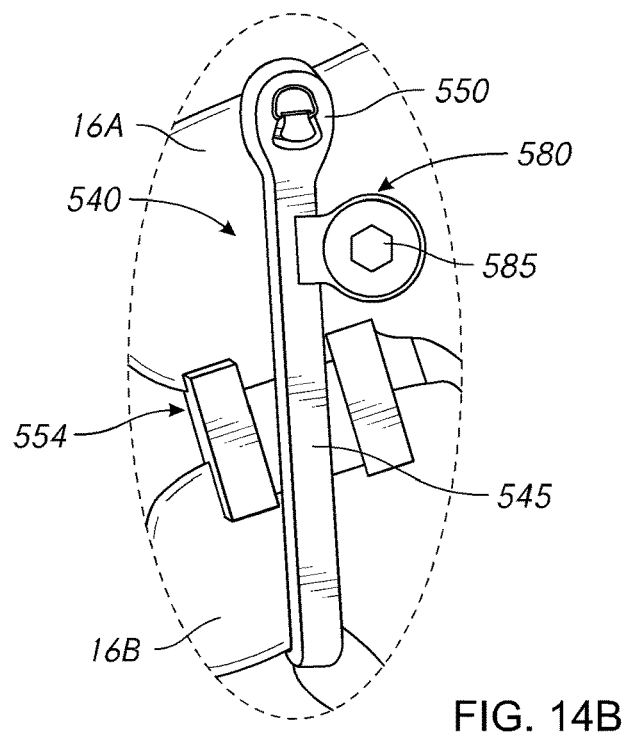
FIG. 14B is an enlarged view of a portion of the vertebral column of FIG. 14A identified as region $X_4$.

As shown in FIGS. 14A and 14B, the band 540 can be used to stabilize a first vertebra 4A and a second vertebra 4B via the spinous articular process 16A (also referred to herein as "process 16A") of the first vertebra 4A and the spinous articular process 16B (also referred to herein as "process 16B") of the second vertebra 4B. More specifically, the lumen 566 of the fastener mechanism 550 can receive the distal end portion 548 of the band 540 such that the body portion 545 forms a loop that substantially encircles the process 16A of the first vertebra 4A and the process 16B of the second vertebra 4B (as described in detail above). The fastener 585 can be inserted into the aperture 582 (FIGS. 13A-13C) and advanced into the process 16A of the first vertebra 4A to affix the anchor portion 580 thereto.

With the anchor portion 580 affixed to the process 16A via the fastener 585, movement of the band 540 in the anterior and/or posterior direction, relative to the process 16A is substantially limited. In addition, a spacer 554 can be disposed between the process 16A of the first vertebra 4A and the process 16B of the second vertebra 4B. The spacer 554 can be similar to the spacer 554 described above with reference to FIGS. 9A-10B. Therefore, the form of spacer 554 is not described in detail herein. As described above, the spacer 554 can reduce slippage of the band 540 relative to the process 16A and/or process 16B that may occur during tightening of the band 540.

While the anchor portion 580 is shown extending from a particular side of the band 540 in FIGS. 13A-14B, in other embodiments, an anchor portion can extend from either side of a band. Moreover, while the band 540 is shown in FIGS.

13A-14B as including a single anchor portion 580, in other embodiments, a band can include a first anchor portion extending from a first side of the band and a second anchor portion extending from a second side, opposite the first side, of the band. In such embodiments, the first anchor portion and the second anchor portion can be aligned along a length of a band or the first anchor portion and the second anchor portion can be offset along the length of the band.

Figure 15:
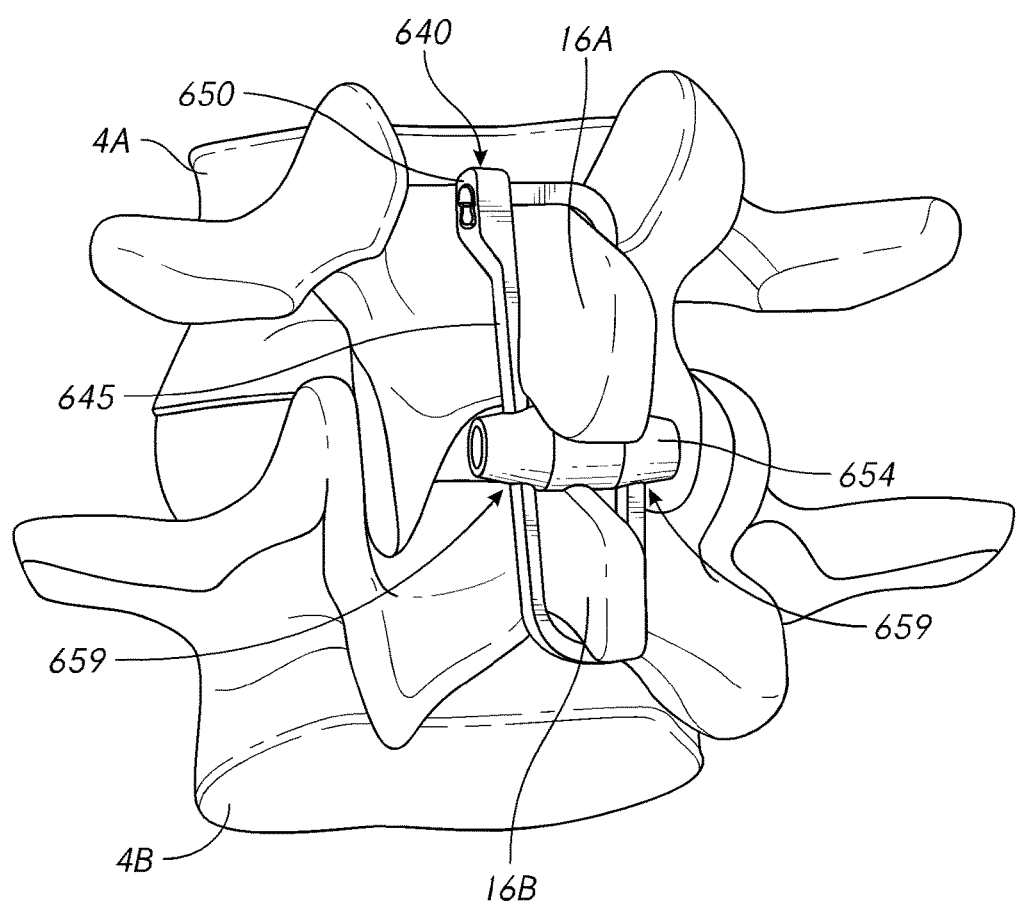
FIG. 15 is a posterior perspective view of a portion of the vertebral column depicting a stabilized vertebra including a flexible elongate body and a spacer, according to an embodiment.

FIG. 15 illustrates a flexible elongate body 640 (also referred to herein as "band"), and a spacer 654 collectively used to stabilize adjacent vertebrae according to an embodiment. While not shown in FIG. 15, flexible elongate body can be used with an anchor, such as, for example, an anchor 280, anchor 380 and/or anchor 480, as shown and described above. As shown in FIG. 15, the band 640 can be used to stabilize a first vertebra 4A and a second vertebra 4B via the spinous articular process 16A (also referred to herein as "process 16A") of the first vertebra 4A and the spinous articular process 16B (also referred to herein as "process 16B") of the second vertebra 4B. The band 640 can be similar to band 140 described above with reference to FIG. 7 and can include similar components. By way of example, band 640 includes a fastener mechanism 650, a body portion 645, and a distal end portion (not shown). Unlike FIGS. 9A-10B, which depict a spacer having indentations and channels, spacer 654 can be substantially cylindrical in shape, and can include a first lumen 659 to receive a portion of band 640, and a second lumen 659 to receive a second portion of band 640. Similar to the spacer 354, the spacer 654 is disposed between the process 16A of the first vertebra 4A and the process 16B of the second vertebra 4B. The spacer 654 can be any suitable shape, size, or configuration. In some embodiments, the diameter of the spacer 654 can be associated with a desired distance between the process 16A of the first vertebra and the process 16B of the second vertebra 4B. Similar to spacer 354, when the band 640 is tightened, the spacer 654 can be configured to limit the tightening of the band 640 such that the desired distance between the process 16A and the process 16B is retained.

Referring now to FIG. 16, a flowchart illustrates a method 790 for stabilizing a first bone portion and a second bone portion. The method 790 includes disposing a flexible band into contact with a first bone portion and into contact with a second bone portion, at 792. In some embodiments, the flexible band can be, for example, a flexible elongate body such as the flexible elongate body 340 described above with reference to FIGS. 9A-10B. The flexible band can define an aperture configured to receive a fastener that can secure the flexible band to the first bone. The fastener can be any suitable fastener such as, for example, a mechanical fastener (e.g., a pin, a nail, a screw, a bolt, a staple, or the like), a chemical fastener (e.g., an adhesive, tape, or the like), or any other suitable fastener or combination thereof.

The method 790 includes advancing a portion of the flexible band through an attachment connection until the first bone portion and the second bone portion are stabilized, at 794. The attachment portion can be substantially similar to the attachment portion (e.g., the fastener mechanism) 340 described herein. The advancing of the portion of the band through the attachment connection can be such that, for example, the band tightens about the first bone portion and about the second bone portion to move the first bone portion from a first orientation relative to the second bone portion to a second orientation relative to the second bone portion. Moreover, the second orientation of the first bone portion relative to the second bone portion can correspond to a stabilized orientation of the first bone portion and the second bone portion. In some embodiments, the first bone portion and the second bone portion can be a portion of a first vertebra and a portion of a second vertebra, respectively. For example, in some embodiments, the first bone portion and the second bone portion can be a spinous articular process of a first vertebra and a spinous articular process of a second vertebra, respectively. In other embodiments, the first bone portion and the second bone portion can be a transverse articular process of a first vertebra and a transverse articular process of a second vertebra, respectively.

In some embodiments, a spacer can be optionally disposed between the first bone portion and the second bone portion to facilitate the stabilization. For example, in some embodiments, the spacer can define a channel configured to receive a portion of the flexible band, thereby limiting or reducing slippage of the flexible band relative to the first bone portion and/or the second bone portion. In some embodiments, a spacer can define a desired distance between the first bone portion and the second bone portion.

The method further includes advancing a portion of the fastener through an aperture and into the first bone portion until the flexible band is secured to the first bone portion, at 796. In some embodiments, the fastener can be advanced through a pre-drilled hole in the first bone portion. In other embodiments, the fastener can be a self-taping fastener such as, for example, a self-taping screw. In this manner, the fastener can substantially limit slippage of the flexible band relative to the first bone portion and or the second bone portion.

Any of the embodiments, described above can be packaged independently or in any suitable combination. For example, in some embodiments, a kit can include at least flexible elongate body (e.g., a band) and a fastener. The band can include an interface portion configured to receive the fastener. For example, the band can be similar to or the same as the band 440 described above with reference to FIGS. 11A-12B. In this manner, the flexible band is configured to stabilize a first bone portion and a second bone portion. The fastener is configured to anchor the flexible band to the first bone portion such that the first bone portion, the second bone portion, and the flexible band are stabilized after being anchored. In some embodiments, the kit can include multiple fasteners of differing kinds. For example, in some embodiments, the kit can include a first fastener that is a bolt and include a second fastener that is a staple. In this manner, the kit can include multiple fasteners configured for use with varying bone structures. By way of example, in some embodiments, the relatively small size of a staple can be suitable for use on a cervical vertebra while the relatively large size of a bolt can be suitable for use on a lumbar vertebra.

In some embodiments, the kit can include a spacer and/or implant. For example, in some embodiments, the kit can include a spacer that is similar to or the same as the spacer 354 described above with reference to FIGS. 9A-10B. In some embodiments, the kit can include a set of spacers where each spacer has a size different than the other spacers included in the set. For example, in some embodiments, the kit can include (1) a first spacer, having a first size and that is configured to be disposed between a spinous articular process of a first cervical vertebra and a spinous articular process of a second cervical vertebra, and (2) a second spacer having a second size greater than the first size and that is configured to be disposed between a spinous articular process of a first lumbar vertebra and a spinous articular process of a second lumbar vertebra. In this manner, the appropriately sized spacer can be selected to stabilize a first and second vertebra.

While various embodiments have been described above, it should be understood that they have been presented by way of example only, not limitation, and various changes in form and details may be made. For example, while the embodiments are illustrated here as being disposed about a spinous articular process of a first vertebra and a spinous articular process of a second vertebra, in other embodiments, a flexible elongate body (e.g., a band) can be disposed about another portion of one or more vertebra. For example, in some embodiments, a flexible elongate body can be dispose about a transverse articular process of a first vertebra and a transverse articular process of a second vertebra. In such embodiments, the band can be tightened about the vertebrae to offset or correct misalignment of a portion of the spine (e.g., scoliosis, or the like).

While the descriptions given are with reference to stabilizing vertebra, another bone(s) such as for example, a sternum and/or a rib(s) could be stabilized using the flexible fastening bands described herein. In another example, a flexible fastening band can be used to stabilize and/or fixate an intramedullary (IM) rod or nail. For example, the flexible fastening band can be used at different longitudinal locations along an IM rod or nail, and used to couple adjacent bone portions to the IM rod or nail. In such situations, a given flexible fastening band can fix a first bone portion, the IM rod or nail, and a second bone portion, all of which are positioned between the distal portion and the attachment connection of the flexible fastening band. In yet another example, a flexible fastening band can be used to stabilize and/or fixate a bone fragment. While various embodiments have been described above with regard to natural bone spaces, (e.g., the space between an inferior articulate process and a superior articulate process), in other embodiments, the bone spacing can be man-made (e.g., sternum split during a heart procedure), and/or due to an injury (e.g., broken bone).

Where methods described above indicate certain events occurring in certain order, the ordering of certain events can be modified. Additionally, certain of the events can be performed concurrently in a parallel process when possible, as well as performed sequentially as described above. For example, while the method 790 described above includes advancing a portion of the band into the attachment connection prior to advancing the fastener, in some embodiments, the fastener can be at least partially advanced into a bone portion prior to the portion of the band being advanced through the attachment portion. In some embodiments, at least a portion of the advancing of the fastener into the bone portion and at least a portion of the advancing of the portion of the band into the attachment connection can be done concurrently (e.g., simultaneously or alternatively in relatively small increments).

By way of another example, in some embodiments, a spacer (e.g., the spacer 454 described above with reference to FIGS. 12A and 12B) can be disposed between a first bone portion and a second bone portion prior to tightening a band (e.g., the band 440 described above) about the first bone portion and the second bone portion. For example, in some embodiments, the spacer can be disposed between the first bone portion and the second bone portion after advancing a fastener (e.g., the fastener 485 described above) into the bone portion and prior to inserting a distal end portion of the band into an attachment connection. In other embodiments, the spacer can be disposed between the first bone portion and the second bone portion prior to the insertion of the fastener in the first bone portion and prior to the insertion of the distal end portion into the attachment connection. In still other embodiments, the spacer can be disposed between the first bone portion and the second bone portion after the fastener is completely advanced into the first bone portion and after the band is partially tightened about the first bone portion and the second bone portion.

Any portion of the apparatus and/or methods described herein may be combined in any combination, except mutually exclusive combinations. The embodiments described herein can include various combinations and/or sub-combinations of the functions, components and/or features of the different embodiments described.

What is claimed is:

1. A method, comprising:
disposing a flexible band into contact with a first bone portion and into contact with a second bone portion, the flexible band having an aperture configured to receive a fastener that is configured to secure the flexible band to the first bone portion;
advancing a portion of the flexible band through an attachment connection of the flexible band until the first bone portion and the second bone portion are stabilized; and
advancing a portion of the fastener through the aperture and into the first bone portion until the flexible band is secured to the first bone portion, wherein the first bone portion is a spinous process of a first vertebra and the second bone portion is a spinous process of a second vertebra.

2. The method of claim 1, further comprising:
disposing an implant between the first bone portion and the second bone portion, the implant having a channel; and
disposing a portion of the flexible band into the channel of the implant.

3. The method of claim 1, wherein the fastener is a screw, the portion of the fastener includes a threaded portion of the screw.

4. The method of claim 1, wherein flexible band includes a flexible elongate body that is (1) monolithically formed with the attachment connection and (2) separately formed from an anchor of the flexible band that includes the aperture.

5. The method of claim 4, wherein disposing the flexible band includes:
disposing the anchor about the portion of the flexible elongate body and into contact with the first bone portion.

6. The method of claim 1, further comprising advancing the portion of the flexible band through the attachment connection of the flexible band such that the first bone portion is moved from a first orientation relative to the second bone portion to a second orientation relative to the second bone portion.

7. A method, comprising:
disposing a flexible band into contact with a first bone portion and into contact with a second bone portion, the flexible band having an aperture configured to receive a fastener that is configured to secure the flexible band to the first bone portion, wherein the flexible band includes a flexible elongate body having a centerline between a proximal end of the flexible elongate body and a distal end of the flexible elongate body, the aperture is substantially centered along the centerline;

advancing a portion of the flexible band through an attachment connection of the flexible band until the first bone portion and the second bone portion are stabilized; and advancing a portion of the fastener through the aperture and into the first bone portion until the flexible band is secured to the first bone portion.

8. A method, comprising:

disposing a flexible band into contact with a first bone portion and into contact with a second bone portion, the flexible band having an aperture configured to receive a fastener that is configured to secure the flexible band to the first bone portion;

advancing a portion of the flexible band through an attachment connection of the flexible band until the first bone portion and the second bone portion are stabilized; and advancing a portion of the fastener through the aperture and into the first bone portion until the flexible band is secured to the first bone portion, wherein the first bone portion is a first transverse process of a first vertebra, the second bone portion is a second transverse process of a second vertebra.

9. A method, comprising:

disposing an implant between the first bone portion and a second bone portion;

positioning a flexible band relative to a first bone portion and a second bone portion, wherein the flexible band comprises a distal end portion, a body portion located proximal to the distal end portion, and an attachment connection located proximal to the body portion;

positioning an anchor portion comprising an aperture relative to the first bone portion;

advancing the distal end of the flexible band through the attachment connection of the flexible band, wherein the flexible band is at least partially tightened about the first bone portion and the second bone portion; and advancing a fastener through the aperture and into the first bone portion.

10. The method of claim 9, wherein the implant comprises a surface having a barrier configured to prevent the body portion of the flexible band from sliding.

11. The method of claim 9, wherein the aperture has a longitudinal axis that is generally perpendicular to a longitudinal axis of the flexible band when the flexible band is substantially flat.

12. The method of claim 9, wherein the flexible band comprises a longitudinal axis, wherein the aperture is located along the longitudinal axis.

13. The method of claim 9, wherein the flexible band comprises a longitudinal axis, wherein the aperture is offset from the longitudinal axis.

14. The method of claim 9, wherein advancing the distal end of the flexible band through the attachment connection comprises advancing the distal end of the flexible band through the attachment connection in only one direction.

15. The method of claim 9, wherein the anchor portion is movable along the flexible band.

16. The method of claim 9, wherein the anchor portion is disposed about the distal end portion and/or the body portion prior to inserting the distal end portion through the attachment connection.

17. The method of claim 9, wherein the anchor portion is fixed relative to the flexible band.

18. The method of claim 9, wherein the first bone portion is a portion of a first vertebra and the second bone portion is a portion of a second vertebra.

* * * * *